US 6,952,603 B2
(12) United States Patent
Gerber et al.

(10) Patent No.: US 6,952,603 B2
(45) Date of Patent: Oct. 4, 2005

(54) SUBCUTANEOUS ANALYTE SENSOR

(75) Inventors: Martin Gerber, Carmel, IN (US); Matthias Essenpreis, Fremont, CA (US); Wolfgang Petrich, Bad Schöhorn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 474 days.

(21) Appl. No.: 09/810,635

(22) Filed: Mar. 16, 2001

(65) Prior Publication Data

US 2002/0161286 A1 Oct. 31, 2002

(51) Int. Cl.$^7$ .............................. A61B 5/00; G01B 9/02
(52) U.S. Cl. ..................................... 600/310; 356/478
(58) Field of Search ................................ 600/310, 300, 600/319, 320, 321, 322, 347, 348, 309, 473, 476, 407, 316; 350/478, 477; 356/39, 478; 435/4, 973; 378/47, 79; 250/440.11

(56) References Cited

U.S. PATENT DOCUMENTS

| 4,140,815 | A | | 2/1979 | Dege et al. | |
|---|---|---|---|---|---|
| 4,670,125 | A | | 6/1987 | Mueller et al. | |
| 5,098,532 | A | | 3/1992 | Thompson et al. | |
| 5,227,040 | A | * | 7/1993 | Simons ....................... | 204/631 |
| 5,246,551 | A | | 9/1993 | Pletcher et al. | |
| 5,408,999 | A | | 4/1995 | Singh et al. | |
| 5,551,422 | A | | 9/1996 | Simonsen et al. | |
| 5,926,269 | A | | 7/1999 | Von Der Eltz et al. | |
| 6,011,984 | A | * | 1/2000 | Van Antwerp et al. ..... | 600/317 |
| 6,026,312 | A | * | 2/2000 | Shemwell et al. .......... | 600/310 |
| 6,049,727 | A | | 4/2000 | Crothall | |
| 6,070,093 | A | | 5/2000 | Oosta et al. | |
| 6,095,974 | A | * | 8/2000 | Shemwell et al. .......... | 600/310 |
| 6,442,410 | B1 | * | 8/2002 | Steffes ........................ | 600/319 |
| 6,611,698 | B1 | * | 8/2003 | Yamashita et al. .......... | 600/310 |
| 6,654,620 | B2 | * | 11/2003 | Wu et al. .................... | 600/310 |

FOREIGN PATENT DOCUMENTS

| DE | 19540456 A1 | 5/1997 |
|---|---|---|
| WO | WO 00/13003 | 3/2000 |

OTHER PUBLICATIONS

Faita, G., De Nora Permalec, "Caustic Soda Without Chlorine Production," Seventh Forum Proceedings, published by the Electrosynthesis Company, Inc. (1993).

Millington, J.P., "An Electrochemical Unit for the Recovery of Sodium Hydroxide and Sulphuric Acid from Waste Streams," Chp. 13, pp. 195–206, from Ion Exchange Membranes, Published for Society of Chemical Industry, London, by Ellis Horwoood Limited Publishers, Chichester (1983).

(Continued)

*Primary Examiner*—Daniel Robinson
(74) *Attorney, Agent, or Firm*—Sujatha Subramaniam; Roche Diagnostics Operations, Inc.

(57) ABSTRACT

Assembly and method for measuring the concentration of an analyte in a biological matrix. The assembly includes an implantable optical-sensing element that comprises a body, and a membrane mounted on the body in a manner such that the membrane and the body define a cavity. The membrane is permeable to the analyte, but is impermeable to background species in the biological matrix. A refractive element is positioned in the cavity. A light source transmits light of a first intensity onto the refractive element, and a light detector receives light of a second intensity that is reflected from the cavity. A controller device optically coupled to the detector compares the first and second light intensities, and relates the intensities to analyte concentration.

30 Claims, 24 Drawing Sheets

OTHER PUBLICATIONS

Soldatkin, A.P., El'skaya, A.V., Shul'ga, A.A., Jdanova, A.S., Dzyadevich, S.V., Jaffrezic–Renault, N., Martelet, C., Clechet, P., "Glucose sensitive conductometric biosensor with additional Naflon membrane: reduction of influence of buffer capacity on the sensor response and extension of its dynamic range," Analytica Chimica Acta 288, 197–203, (1994).

Kohl, M., Essenpreis, M., Cope, M., "The Influence of glucose concentration upon the transport of light in tissue–simulating phantoms," Phys. Med. Biol. 40 , pp. 1267–1287, (1995).

Simons, R., "A novel method for preparing bipolar membranes," Electrochimica Acta, vol. 31, No. 9, pp. 1175–1176, (1986).

Bruulsema, J.T., Hayward, J.E., Farrell, T.J., Patterson, M.S., Heinemann, L., Berger, M., Koschinsky, T., Sandahl–Christiansen, J., Orskov, H., Essenpreis, M., Schmelzeisen–Redeker, G., Bocker, D., "Correlation between blood glucose concentration in diabetics and nonivasively measured tissue optical scattering coefficient," Optics Letters, vol. 22, No. 3, Feb. 1, 1997.

Kohl, M., Cope, M., Essenpreis, M., Bocker, D., "Influence of glucose concentration on light scattering in tissue–simulating phantoms," a reprint from Optics Letters, pp. 2170–2172, (1994).

Arnold, F.H., Zheng, W., Michaels, A.S., "A membrane–moderated, conductimetric sensor for hte detection and measurement of specific organic solutes in aqueous solutions," Journal of Membrane Science 167, pp. 227–239, (2000).

Kang, S., Lin, H., Day, D.E., and Stoffer, J.O., "Optically transparent polymethyl methacrylate composites made with glass fivers of varying refractive index," *Journal of Materials Research*, vol. 12, No. 4, 1997.

* cited by examiner

SUBCUTANEOUS ANALYTE SENSOR

BACKGROUND OF THE INVENTION

The present invention relates to implantable sensors, and more specifically, to implantable sensors for monitoring levels of analytes, such as glucose.

Several designs for implantable sensors that allow continuous in vivo monitoring of levels of analytes such as glucose have been previously described. Many such designs are based on electrochemical analyte detection principles. As such, they are prone to inherent signal instability of the sensor, and they require that chemicals (e.g., enzymes and mediators) be introduced into the patient's body.

A second approach involves physical (i.e. reagent-free) methodology. A review of physical methods for determinations of glucose in vivo is given in J. D. Kruse-Jarres "Physicochemical Determinations of glucose in vivo," J. Clin. Chem. Clin. Biochem. 26 (1988), pp. 201–208. Nuclear magnetic resonance (NMR), electron spin resonance (ESR), and infrared (IR) spectroscopy are named, among others, as non-invasive methods. However, none of these methods has as yet acquired practical significance. Some of them require large and expensive apparatus, generally unsuitable for routine analysis and home monitoring of a patient.

Nearly all of the methods of this second approach are based on spectroscopic principles. Concerning the optical methods, the fundamental principle frequently is the interaction of the irradiated primary light (of a specific wavelength) with the vibration and rotation states of the molecules undergoing analytical determination. The basic vibrational and rotational states of glucose are found in the IR region at wavelengths above 2500 nm. This spectral region is not suitable for invasive analytical determination of glucose because of the strong absorption of water, which is present in high concentration in biological matrices. In the near infra-red (NIR) region, the absorption of water is smaller (the so-called "water transmission window). The spectral analysis of glucose in this region is based on absorption by overtones and combination oscillations of the basic vibrational and rotational states of the glucose molecule (see the article by Kruse-Jarres cited above and EP-A-0 426 358).

Developing a practical implantable glucose sensor on the basis of these principles presents certain problems. These problems result particularly from the fact that the effective signal (the change in the absorption spectrum due to a change in glucose concentration) is generally very small. Sensitivity is always an issue in absorption measurements because of the difficulty in observing a small effective signal superimposed on a relatively much larger background signal. However, in this case the difficulty is enhanced due to background signals resulting from the spectral absorption of water. Some attempts have been made to solve this problem (see e.g., EP-A-0 160 768; U.S. Pat. No. 5,028,787; and WO 93/00856); however, these attempts have not been successful in providing a practical and functional implantable glucose sensor based on absorption principles.

Methods of continuously monitoring glucose based on light scattering principles have also been described. For instance, European patent 0 074 428 describes a method and device for the quantitative determination of glucose by laser light scattering. The method assumes that glucose particles scatter light rays transmitted through a test solution, and that the glucose concentration can be derived from this scattering. The method requires measurement of the spatial angular distribution of the transmitted (i.e. forward-scattered) light emerging from a test cuvette or an investigated part of the body. In particular, the intensity of the transmitted light is measured in an angular region in which the change in relation to the glucose concentration is as large as possible. This intensity is then compared with the intensity measured for the central ray passing directly through the sample. For in vivo analytical determination, a transmission measurement on ear lobes with laser light is exclusively recommended.

A second method based on light scattering principles relies on the measurement of back-scattered light rather than transmitted (i.e. forward-scattered) light. U.S. Pat. No. 5,551,422 describes a method for determining glucose concentration in a biological matrix by performing at least two detection measurements. In each detection measurement, primary light is irradiated into the biological matrix through a boundary surface thereof at a defined radiation site. The light is propagated along a light path within the biological matrix. An intensity of the light is measured as the light emerges as secondary light through a defined detection site of the boundary surface. At least one of the detection measurements is a spatially resolved measurement of multiply scattered light. The detection site is located relative to the irradiation site such that light which was multiply scattered at scattering centers in the biological matrix is detected. The light paths of the at least two detection measurements within the biological matrix are different. Glucose concentration is then derived from the dependence of the intensity of the secondary light on the relative positions of the irradiation site and the detection site.

Additional methods are needed which minimize or eliminate the effect on light intensity from variations of physical parameters, such as temperature and/or changes in the concentrations of background ions, proteins, and organic acids in the biological matrices, and which minimize the number of light paths and/or detection measurements required to be performed.

BRIEF SUMMARY OF THE INVENTION

The present invention, in one form thereof, comprises an assembly for measuring the concentration of an analyte in a biological matrix. The assembly includes an implantable optical-sensing element, a source for transmitting light into the optical-sensing element, and a detector for receiving light emitted from the optical-sensing element. A signal-processing and computing element is provided to compare the respective amounts of transmitted and emitted light, and relate these amounts to the concentration of the analyte in the biological matrix. The implantable optical-sensing element comprises a body and a membrane mounted on the body, such that the membrane and the body define a cavity. The membrane is substantially permeable to the analyte, and substantially impermeable to background species in the biological matrix, such that the analyte is received in the cavity. A refractive element for the transmitted light is positioned in the cavity.

The present invention, in another form thereof, comprises an implantable optical-sensing element suitable for measuring the concentration of an analyte in a biological matrix. The optical-sensing element comprises a body, and a membrane mounted on the body such that the body and the membrane define a cavity for receiving the analyte. The membrane is substantially permeable to the analyte, and substantially impermeable to background species in the biological matrix, such as large proteins. A refractive element having a refractive index different from the refractive index of the analyte is disposed in the cavity.

The present invention, in yet another form thereof, comprises an assembly for measuring the concentration of an analyte in a biological matrix. The assembly comprises an implantable optical-sensing element comprising a body, and a first semi-permeable membrane mounted on the body to define a cavity. The first semi-permeable membrane is permeable to the analyte, and impermeable to background species in the biological matrix. A second membrane is mounted on the body remote from the first membrane to define a second cavity. A first refractive element is disposed in the first cavity, and a second refractive element is disposed in the second cavity. A light source provides light into each of the first and second cavities toward the respective first and second refractive elements, and a light detector receives light from each of the first and second cavities. A signal processor and computer are provided to relate the respective intensities of the provided light and the received light to the analyte concentration.

The present invention, in still another form thereof, comprises an implantable optical-sensing element suitable for measuring the concentration of an analyte in a biological matrix. The optical-sensing element comprises a body and a first semi-permeable membrane mounted on the body. The first membrane is permeable to the analyte, and impermeable to background species in the biological matrix. The first membrane and the body are aligned to define a first cavity, the first cavity having a first refractive element disposed therein. A second membrane is mounted on the body remote from the first membrane. The second membrane and the body are aligned to define a second cavity isolated from the first cavity, the second cavity having a second refractive element disposed therein.

The present invention, in yet another form thereof, comprises a method for measuring the concentration of an analyte in a biological matrix. An optical-sensing element is implanted in the biological matrix, the optical-sensing element comprising a body and a semi-permeable membrane mounted on the body, the semi-permeable membrane being permeable to the analyte and impermeable to background species in the matrix. The semi-permeable membrane and the body define a cavity, and a refractive element is disposed in the cavity. Primary light from a light-emitting source is introduced into the body of the optical-sensing element, and is directed toward the refractive element. Secondary light reflected from the optical-sensing element is collected and transmitted to a light-detecting device. The intensity of the secondary light is measured, and the analyte concentration in the biological matrix is determined by comparing the intensity of the secondary light with the intensity of the primary light.

The present invention, in a still further form thereof, comprises a method for measuring the concentration of an analyte in a biological matrix. An optical-sensing element is implanted in the biological matrix, the optical-sensing element comprising a body, a first membrane mounted on the body, and a second membrane mounted on the body remote from said first membrane. At least one of the membranes is permeable to the analyte and impermeable to background species in the biological matrix. The first and second membranes define a cavity, and a refractive element is disposed in the cavity. Primary light from a light-emitting source is transmitted into the cavity toward the refractive element, and secondary light reflected from the refractive element is collected and transmitted to a light-detecting device. The intensity of the secondary light is measured with the light-detecting device, and the analyte concentration in the biological matrix is derived therefrom.

The present invention, in another form thereof, comprises a method for measuring the concentration of an analyte in a biological matrix. An optical-sensing element is implanted in the biological matrix, the optical-sensing element comprising a body, a first semi-permeable membrane mounted on the body, and a second semi-permeable membrane mounted on the body remote from the first semi-permeable membrane. The body and the first membrane define a cavity having a first refractive element disposed therein, and the body and the second membrane define a second cavity isolated from the first cavity and having a second refractive element disposed therein. Primary light from a light-emitting source is transmitted into the body, and respective streams of the primary light are directed into the first cavity toward the first refractive element, and into the second cavity toward the second refractive element. Light reflected from the first refractive element is collected and transmitted to a first channel of a light-detecting device, and light from the body reflected at the second refractive element is collected and transmitted to a second channel of the light-detecting device. The respective intensities of light collected from each of the first and second channels is measured, and the concentration of an analyte in the biological matrix is computed by comparing the intensity of the transmitted light and the light collected from each of the first and second channels.

The present invention, in yet another form thereof, comprises an assembly for monitoring the concentration of an analyte in a biological matrix. The assembly includes an implantable optical-sensing element that comprises a body, a membrane mounted on the body, and a refractive element disposed in a cavity defined by the membrane and the body. The analyte is received in the cavity through the membrane, wherein the membrane is substantially permeable to the analyte of interest and substantially impermeable to background species in the biological matrix. One or more light sources provide light of a first wavelength and a second wavelength into the cavity, the refractive element in the cavity having a refractive index greater than the refractive index of the analyte at the first wavelength, and less than the refractive index of the analyte at the second wavelength. A detector receives from the cavity an intensity of light at each of the first and second wavelengths at a first concentration of said analyte, and receives an intensity of light at each of the first and second wavelengths at a second concentration of the analyte. A signal-processing and computing element is optically coupled to the detector for comparing the intensities of light received at the first wavelength to the intensities of light received at the second wavelength, and for relating the intensities to analyte concentration.

The present invention, and yet another form thereof, comprises a method for monitoring a change in the concentration of an analyte in a biological matrix of a test subject. An optical-sensing element is implanted in the test subject, the implantable optical-sensing element comprising a body and a membrane mounted on the body, wherein the membrane and body define a cavity for receiving the analyte. The membrane is substantially permeable to the analyte of interest and substantially impermeable to background species in the biological matrix. A refractive element is disposed in the cavity. Light of a first wavelength and a second wavelength is introduced into the cavity, wherein the refractive element has a refractive index greater than the refractive index of the analyte at the first wavelength, and less than the refractive index of the analyte at the second wavelength. An intensity of light at each of the first and second wavelengths is measured at a first concentration of the analyte, and an intensity of light at each of said first and second wavelengths is measured at a second concentration of the analyte. The change in concentration of the analyte is computed by comparing the intensities of light received at the first wavelength to the intensities of light received at the second wavelength for each of the first and second concentrations, and relating the intensities to changes in analyte concentration.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION OF THE INVENTION

Figure 1:
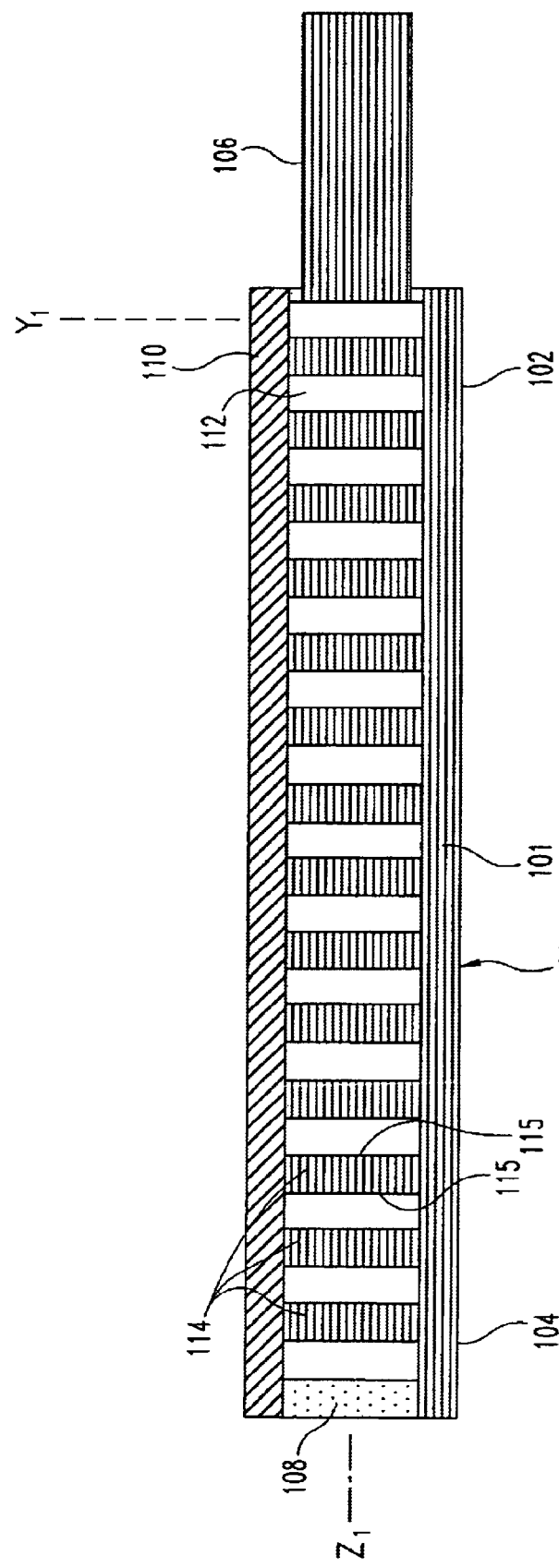
FIG. 1 shows a side cross-sectional view through the $Y_1Z_1$-plane of an optical-sensing element according to a first embodiment of the present invention.

As used herein, the term "biological matrix" denotes a body fluid or a tissue of a living organism. Biological matrices, to which the invention relates, are optically heterogeneous, that is, they contain a large number of substances (e.g., salts, proteins, and organic acids) which can affect the refractive index.

As used herein, the term "background species" refers to analytes such as ions, proteins, and organic acids native to a biological matrix, or to non-native agents introduced therein, that are capable of undergoing a change of refractive index substantially as a result of (1) adequate variations in concentration in vivo, and (2) a large specific refractive index increment. "Background species" does not refer to the analyte(s) being monitored.

As used herein, the term "refractive element" is used to refer to an element having a refractive index different from the refractive index of the medium to be measured.

As used herein, the term "mMol" denotes the concentration of a substance in units of millimoles per liter.

As used herein, the term "n" denotes the refractive index of a substance.

The present invention provides an assembly comprising an implantable optical-sensing element suitable for measuring the concentration of an analyte in a biological matrix. The function of the optical-sensing element is to generate changes in light refraction, which changes are a function of changes in the concentration of the analyte in the biological matrix. The optical-sensing element includes a membrane mounted on a body, such that the membrane and the body define a cavity. The membrane is substantially permeable to the analyte, thereby permitting the analyte to pass through the membrane and into the cavity by means such as diffusion or osmosis, and is substantially impermeable to background species in the biological matrix.

The optical-sensing element of the present invention is stable over extended periods of time, does not require frequent recalibration, and does not require signal amplification through enzymatic reactions. The optical-sensing element also minimizes or eliminates background drift in such measurements due to variations in physical parameters such as temperature and/or changes in the concentrations of background ions, proteins, and organic acids that may be present in the biological matrix.

An example of an analyte suitable for monitor utilizing the assembly of the present invention is glucose. It is well known that a change in concentration of an analyte, such as glucose, in a test solution results in a change in the refractive index of the solution. For example, the refractive-index increment of an aqueous glucose solution $\Delta n_m$ for visible wavelengths is $\Delta n_m = 2.5 \times 10^{-5}$/mMol glucose (see R. C. Weast, ed., CRC Handbook of Chemistry and Physics, $55^{th}$ ed. (CRC, Cleveland, Ohio 1974), p. D-205), and this relationship is assumed to be approximately the same over the entire wavelength region under investigation. In other words, the refractive index of a solution rises by approximately $2.5 \times 10^{-5}$ for an increase of one mMol in glucose concentration.

Unfortunately, direct measurement of the glucose concentration in a biological matrix based on a change in refractive index is impractical because refractive index is not per se glucose specific. As shown in Table 1, the presence of certain background molecules (e.g., organic acids) and ions (e.g., sodium and chloride) commonly found in biological matrices can substantially affect the refractive index of the matrix.

TABLE 1

| Substrate | Concentration (mMol) | | | $\Delta n_m$/mMol |
| --- | --- | --- | --- | --- |
| | Plasma | Extracellular | intracellular | |
| glucose | 5 | 5 | 0 | 2.5E-05 |
| $Na^+$ | 142 | 144 | 10 | 5.0E-06 |
| $K^+$ | 4 | 4 | 160 | 5.0E-06 |
| $Ca^{2+}$ | 5 | 3 | 2 | 5.0E-06 |
| $Mg^{2+}$ | 2 | 2 | 25 | 1.3E-05 |
| $Cl^-$ | 102 | 114 | 2 | 5.0E-06 |
| $HCO_3^-$ | 26 | 30 | 10 | 5.0E-06 |
| $PO_4^{3-}$ | 2 | 2 | 100 | 9.0E-06 |
| $SO_4^{2-}$ | 1 | 1 | 20 | 1.0E-05 |
| organic acids | 5 | 5 | 0 | 6.0E-06 |

(Concentration expressed in % w/v)

Independent concentration changes in these species could interfere with the glucose measurement and result in drift or erroneous readings.

The present invention addresses this problem by providing an optical-sensing element having a substantially impermeable body that is enclosed on at least one surface thereof by a semi-permeable membrane. The semi-permeable membrane is designed to exclude undesired background molecules and/or ions from entering/exiting the interior of the body, while allowing the analyte or analytes of interest to freely diffuse through the membrane. When the analyte of interest is glucose, the glucose diffuses through the membrane to equilibrate with tissue glucose concentration. Background species cannot permeate through the membrane. For example, proteins can be excluded by using membranes with adequate pore size (e.g., 30 kD to exclude albumin but enable glucose diffusion), and ions can be excluded by using a polarized membrane (+/−) layer.

It is preferred to use a bipolar membrane as the semi-permeable membrane. Bipolar membranes are ion exchange membranes constructed of two adjoining layers of ion exchangers of opposite polarity (i.e. a cation-exchange side and an anion-exchange side). The charge density of these membranes is such that ions of the same charge as the fixed charges are hindered from diffusing through the membrane. Bipolar membranes are useful for isolating one ionic environment from another. These membranes are highly hydrated, and are thus permeable to non-charged solutes, such as glucose, which can diffuse from one side to the other.

Suitable bipolar membranes for use in the present invention include those produced by Tokuyama Soda (Japan) under the trade name of NeoSepta, available from Electrosynthesis Company, Lancaster, N.Y. These membranes are produced for bulk electrolysis and salt-splitting applications, and thus are mechanically very stable and rigid. They possess the high charge densities required for use in the high salt concentrations of biological matrices. These membranes are approximately 250 um in thickness, and may be cut to any appropriate size. Thinner membranes of lower ionic content could also be used. Thinner membranes are advantageous because they decrease the response time of the sensor and may provide more accurate results.

During use, the semi-permeable membrane must be bonded to the body of the optical-sensing element in a manner that prevents infusion of solution in or out of the interior of the body except through the membrane. This bonding may be accomplished by any of several methods, including heat or ultrasonic bonding, adhesive bonding with pressure-sensitive adhesives or liquid adhesives such as cyanoacrylates (e.g., Superglue or Crazyglue), thermoplastic adhesives such as urethanes or hot-melt adhesives, or photocurable adhesives. Preferred bonding methods for in vivo applications include chemical or physical methods such as heat or ultrasonic bonding.

Typical commercial bipolar membranes comprise a cross-linked polystyrene sulfonate for the cation-exchange side bonded to a crosslinked poly(vinyl benzyl trimethyl ammonium chloride) for the anion-exchange side. The membranes are typically supplied in a high concentration (10%) of salt for stabilization, and are equilibrated with a physiological saline solution (1.15 M NaCl) prior to use in the optical-sensing element. The bipolar membranes are preferably cross-linked to an extent that large molecular weight solutes such as proteins and lipids are also excluded from the membrane, and concomitantly, from the volume enclosed by the membrane.

If a thinner bipolar membrane is used to enable a more rapid response time, it may be desirable to combine the bipolar membrane with a third membrane layer capable of excluding macrosolutes. Such a third membrane layer may, for example, be any of the membranes typically used for dialysis applications, such as regenerated cellulose or polyamide membranes. The third membrane layer may be attached to the sensor body, on or around the bipolar membrane, using any of the methods suitable for attaching the bipolar membrane. Alternatively, the third membrane layer may be laminated directly to the bipolar membrane prior to application of the bipolar-membrane to the sensor body. Moreover, the third membrane layer may be formed on the bipolar membrane by a casting process, for example, by dipping the assembled optical-sensing element with bipolar membrane attached into a solution of a membrane-forming polymer, and then drying the element under controlled conditions.

Bipolar membranes can be formed into hollow fibers in the same way that membranes for dialysis and microdialysis are produced, and the membrane fibers slid over the sensor structure and attached with any of the above methods.

The spectroscopic principle relied upon in the present invention is that light is reflected or refracted at changes in refractive index. The closer the refractive indices of two interfacing media, the smaller the specular reflection. When the refractive indices match, no specular reflection is observable. Correspondingly, the specular reflection increases in absolute magnitude as the refractive indices of the two interfacing media become more disparate. However, the relative change in specular reflection is largest when the refractive index differential is small, as discussed in M. Kohl, M. Cope, M. Essenpreis, and D. Böcker, Optics Letters, Vol. 19, No. 24, (1994) pp. 2170–2172, which is incorporated herein by reference in its entirety. Based upon these competing effects, it has been determined that the sensitivity of the measurement is optimized when the refractive index of a refractive element disposed within the body, and the refractive index of an analyte such as glucose are preferably within 9%, more preferably within 5%, of each other when the glucose concentration in the biological matrix is at physiological levels, i.e., between 4 and 7 mMol.

When the analyte of interest is glucose, the refractive element is preferably formed from a material with a refractive index close to that of a glucose solution at physiological concentrations (i.e. n=1.38). Preferably, the refractive element is formed from a moldable plastic having a refractive index between 1.26 and 1.50, more preferably between 1.31 and 1.45. Examples of suitable plastics include poly (undecafluorohexyl acrylate) (n=1.36), poly(decamethylene carbonate) (n=1.47), poly(ethylene succinate), poly (ethylene oxide) (n=1.46), poly(trifluoroethylene) (n=1.34), poly(hexafluoropropylene) (n=1.31), poly(methyl methacrylate) (n=1.49), poly(ethylene) (n=1.49), poly(oxy (diethylsilylene)) (n=1.42), and poly(vinyl fluoride) (n=1.45). Preferred plastics include poly(methyl methacrylate) and poly(ethylene).

Figure 2:
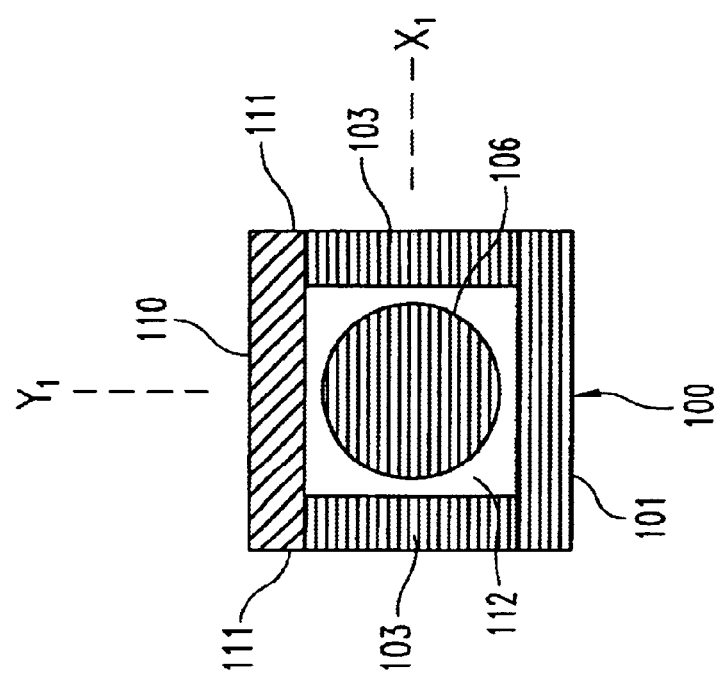
FIG. 2 shows a front cross-sectional view through the $X_1Y_1$-plane of the optical-sensing element illustrated in FIG. 1.
Figure 3:
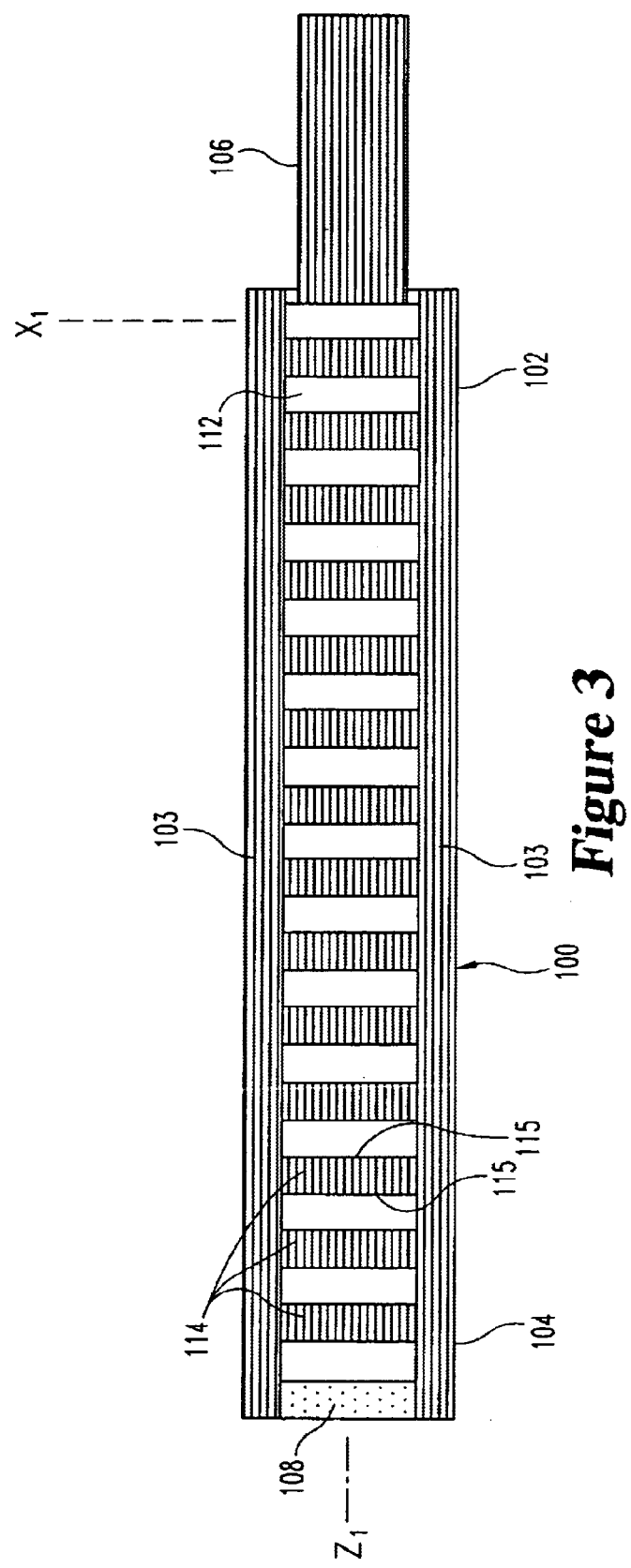
FIG. 3 shows a shows a top cross-sectional view through the $X_1Z_1$-plane of the optical-sensing element illustrated in FIG. 1.

A first embodiment of the optical-sensing element of the invention is illustrated in FIGS. 1–3. The optical-sensing element includes a body 100, a semi-permeable membrane 110 and a refractive element 114. The body 100 and membrane 110 are oriented to define a cavity 112. The refractive element 114 and the analyte or analytes of interest (not shown) are disposed in the cavity 112. The semi-permeable membrane 110 is substantially permeable to the analyte(s), but substantially impermeable to background species in the biological matrix.

Preferably, the body 100 of the optical-sensing element has a generally "U" or "V"-shaped cross-section, and comprises a molded plastic. The body 100 has a base portion 101 and two opposing side walls 103. Each of the side walls 103 includes an upper edge 111. The body 100 has a proximal end 102 and a distal end 104, and is preferably less than 2 mm in length. A light-transmitting conduit 106, here a single optical fiber, is optically coupled to the proximal end 102 of the body. Optical coupling between the body and the conduit can be accomplished by any means known in the art, such as, for example, using an adhesive to secure the conduit 106 in an orifice formed in the body 100.

The refractive element 114 preferably is made from the same material as the body 100 as part of a single plastic molding process. In the embodiment of FIGS. 1–3, the refractive element 114 comprises a plurality of substantially parallel, rectangular plates. The integral, unit-body construction, with bracing by the rectangular plates, gives the optical-sensing element particular stability. Preferably, each individual plate of the refractive element has a thickness less than 10 µm. Each plate has two faces 115 which function as refractive or reflective surfaces. The faces 115 may be flat, or alternatively, may be tilted or even randomly shaped structures (e.g., FIGS. 7, 10 and 13). Tilted plates may be useful to avoid interferences. When faces such as those in FIGS. 1–3 are utilized, the faces 115 are oriented such that each lies in a plane perpendicular to the longitudinal axis of the body 100, and the faces 115 on adjacent plates are preferably separated by no more than 10 µm.

The change in the intensity of light reflected off the refractive element may be maximized by using a refractive element 114 having faces 115 capable of multiple reflection and/or refraction in accordance with the Fresnel formulas. This change may be further maximized by optimizing the refractive index differential between the analyte and the refractive element 114. Preferably, the optical-sensing element includes a refractive element having at least one hundred parallel plates 114 with at least two hundred faces 115. Most of the plates and faces have been omitted from FIG. 1 for clarity. By using multiple faces 115, the intensity of reflected or refracted light corresponding to changes in refractive index (and therefore to changes in analyte concentration) can be amplified by a factor of at least 200.

The body 100 of the optical-sensing element provides a support structure for the optical-sensing element and should correspondingly be rigid or semi-rigid. Since the sensing element is designed to be implanted in living tissue, the construction material of the body 100 should also be biocompatible. The distal end 104 of the body 100 preferably comprises a light absorbing material 108, although a transparent material may alternatively be utilized.

The refractive element 114 can comprise a single structure or a plurality of structures. No particular shape is required. Examples of single structures include a porous fiber, a porous rod, a convoluted ribbon, and a convoluted fiber. The refractive element may also comprise combinations of the foregoing. Examples of pluralities of structures include regular or randomly shaped plates, particles, beads and powders, or combinations of the foregoing. Regardless of the particular embodiment, the refractive element preferably provides a plurality of reflective or refractive faces 115 that interface with the analyte to amplify the reflected light when compared to light reflected from a single surface.

Figure 4:
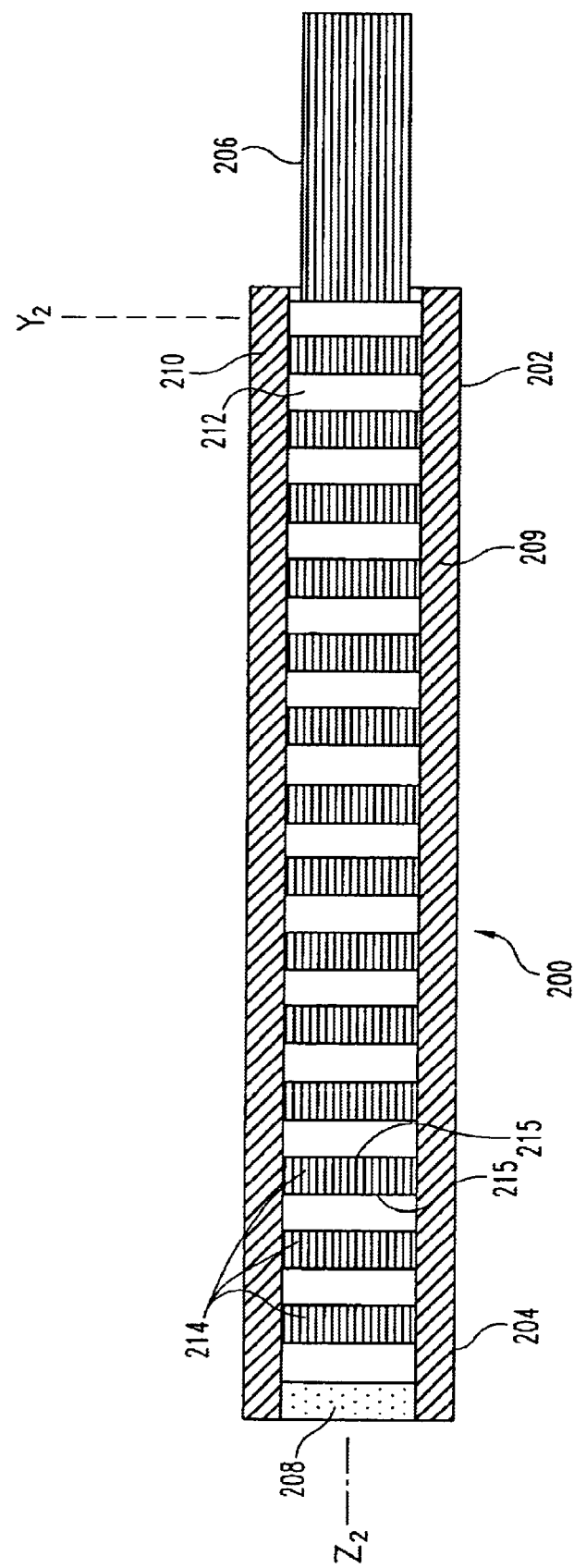
FIG. 4 shows a side cross-sectional view through the $Y_2Z_2$-plane of an optical-sensing element according to a second embodiment of the present invention.
Figure 5:
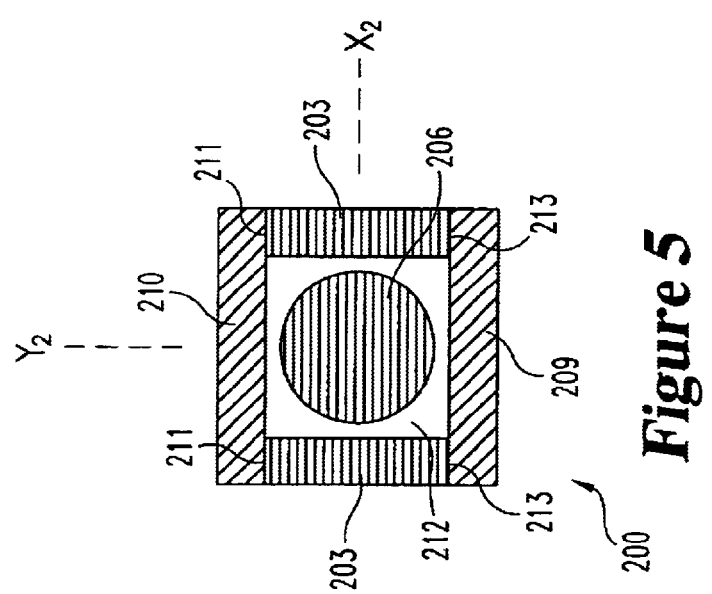
FIG. 5 shows a front cross-sectional view through the $X_2Y_2$-plane of the optical-sensing element illustrated in FIG. 4.
Figure 6:
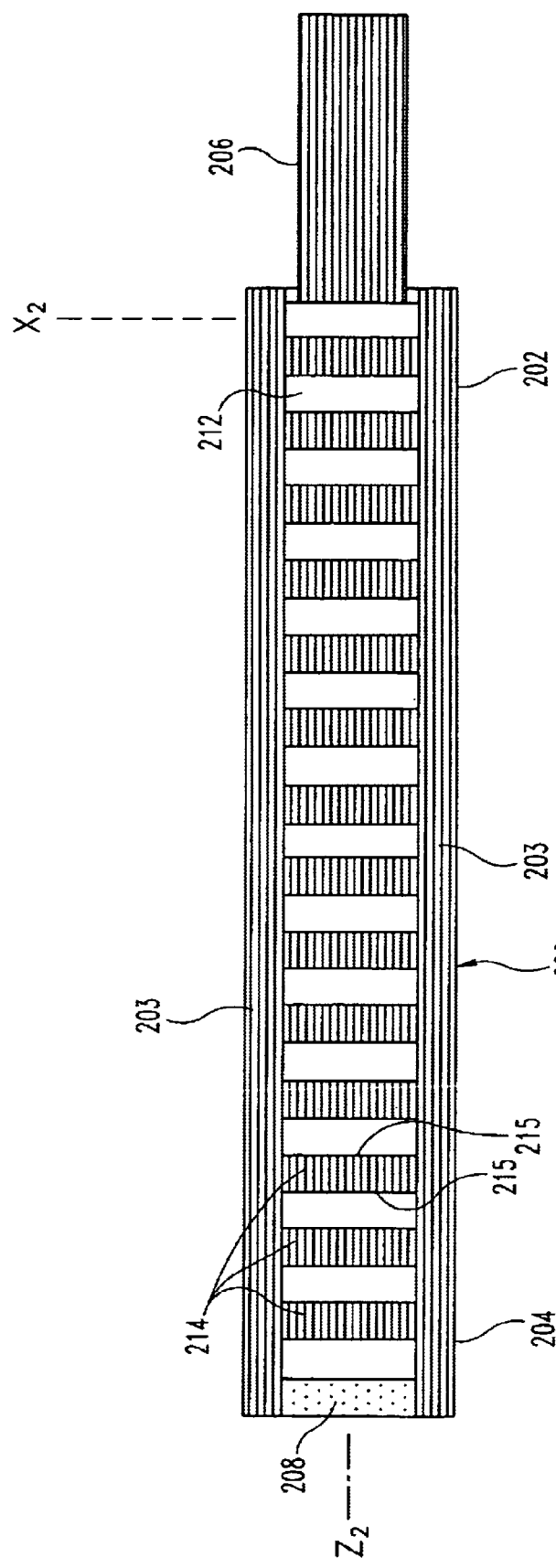
FIG. 6 shows a top cross-sectional view through the $X_2Z_2$-plane of the optical-sensing element illustrated in FIG. 4.

A second embodiment of the invention is illustrated in FIGS. 4–6. The body 200 of the optical-sensing element comprises two parallel, elongated members 203, each having an upper edge 211 and a lower edge 213. The body is preferably formed of molded plastic and is dimensioned in similar manner to the embodiment of FIGS. 1–3. The body 200 also includes a proximal end 202 and a distal end 204. A light-transmitting conduit 206, here a single optical fiber, is sealed in an orifice in the proximal end 202. The distal end 204 preferably comprises a light-absorbing material 208. In this embodiment, a first semi-permeable membrane 210 is attached to the top edges 211 of the elongated members 203, and a second semi-permeable membrane 209 is attached to the bottom edges 213 of the elongated members 203.

The elongated members 203 and semi-permeable membranes 209 and 210 define a cavity 212. The cavity contains the analyte of interest (not shown) and a refractive element 214. The refractive element comprises a plurality of substantially parallel, rectangular plates, and the elongated members 203 are held together with cross-support from the rectangular plates. In other pertinent respects the numbers and orientation of rectangular plates 214 and faces 215 are similar to those as described in the previous embodiment.

Figure 7:
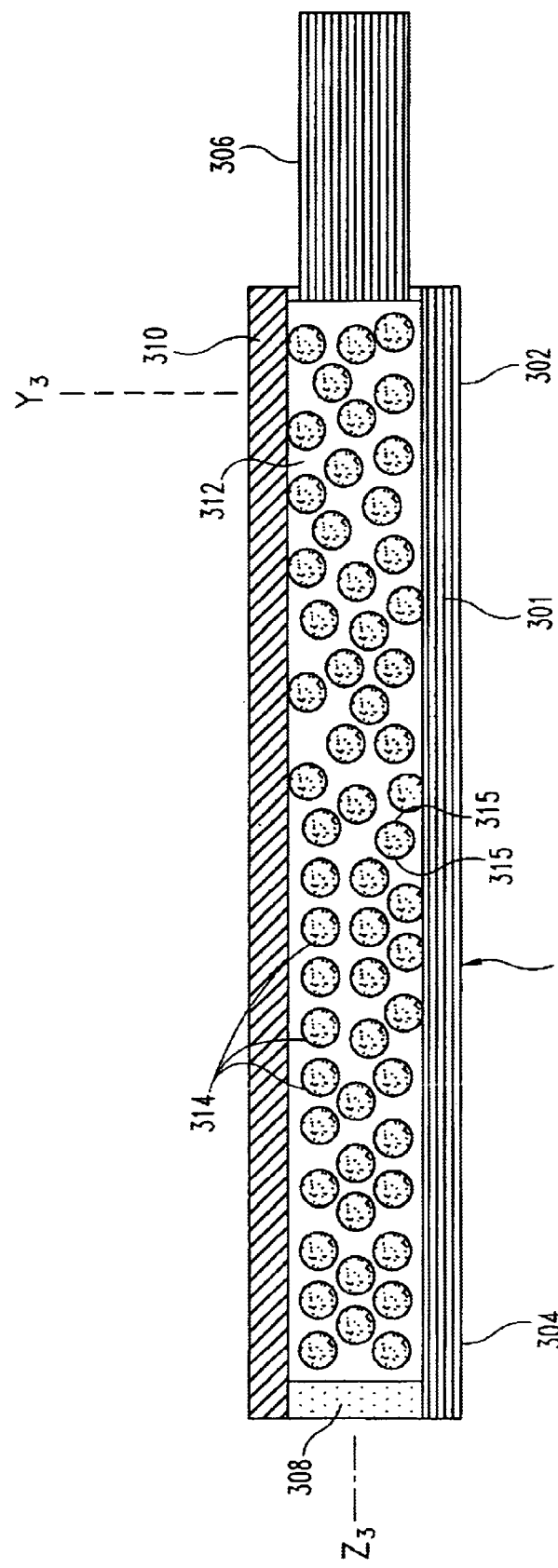
FIG. 7 shows a side cross-sectional view through the $Y_3Z_3$-plane of an optical-sensing element according to a third embodiment of the present invention.
Figure 8:
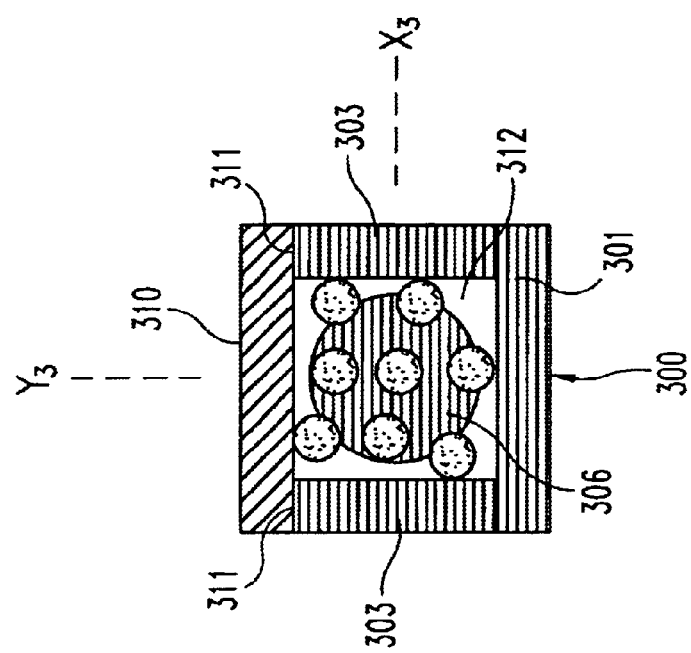
FIG. 8 shows a front cross-sectional view through the $X_3Y_3$-plane of the optical-sensing element illustrated in FIG. 7.
Figure 9:
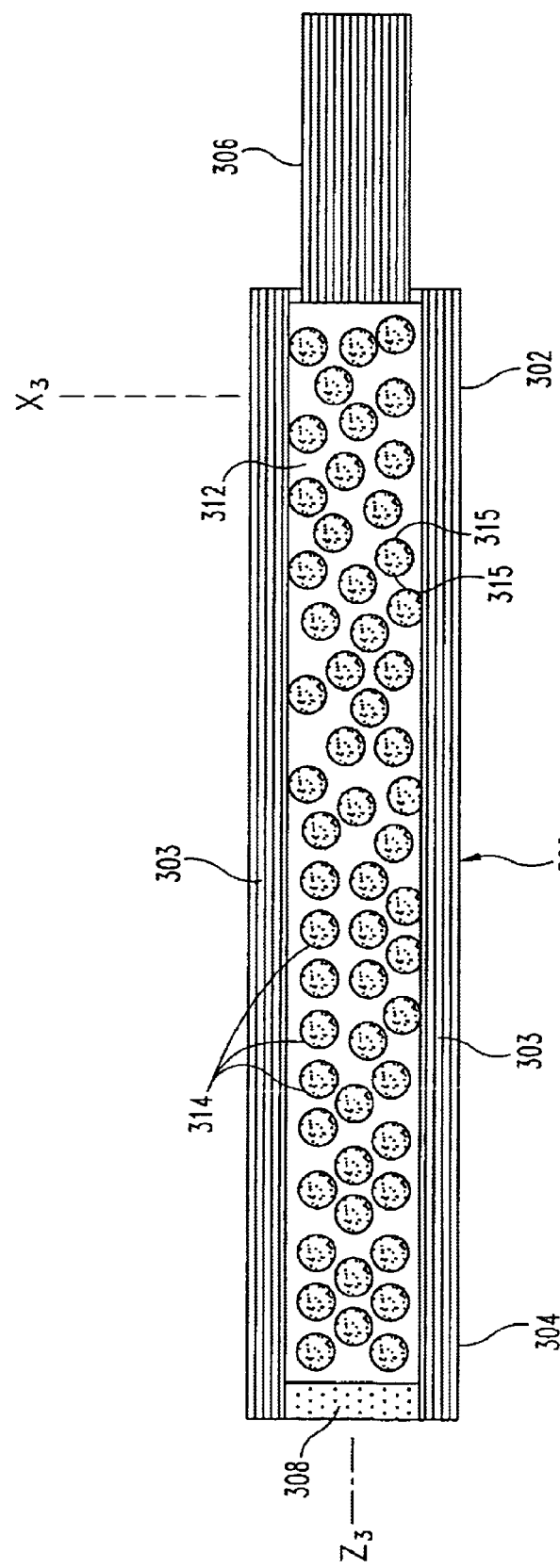
FIG. 9 shows a top cross-sectional view through the $X_3Z_3$-plane of the optical-sensing element illustrated in FIG. 7.

A third embodiment of the invention is illustrated in FIGS. 7–9. In this embodiment, the body 300, base portion 301, side walls 303, light-transmitting conduit 306, light-absorbing material 308, membrane 310, edges 311, cavity 312, and respective proximal and distal ends 302 and 304 are as described in the embodiment of FIGS. 1–3. The refractive element 314 comprises a plurality of beads, which provide a plurality of reflective or refractive surfaces 315. The composition of the beads is normally not important, as long as they provide suitable reflective or refractive surfaces. Glass beads, or beads formed from polymers such as polystyrene, are particularly suitable. The composition, diameter, and number of the beads can be varied to achieve a packing arrangement which provides optimal amplification of light by multiple reflections off the bead surfaces 315. A similar effect is achieved when refractive powders are provided in the cavity in place of the beads.

Figure 10:
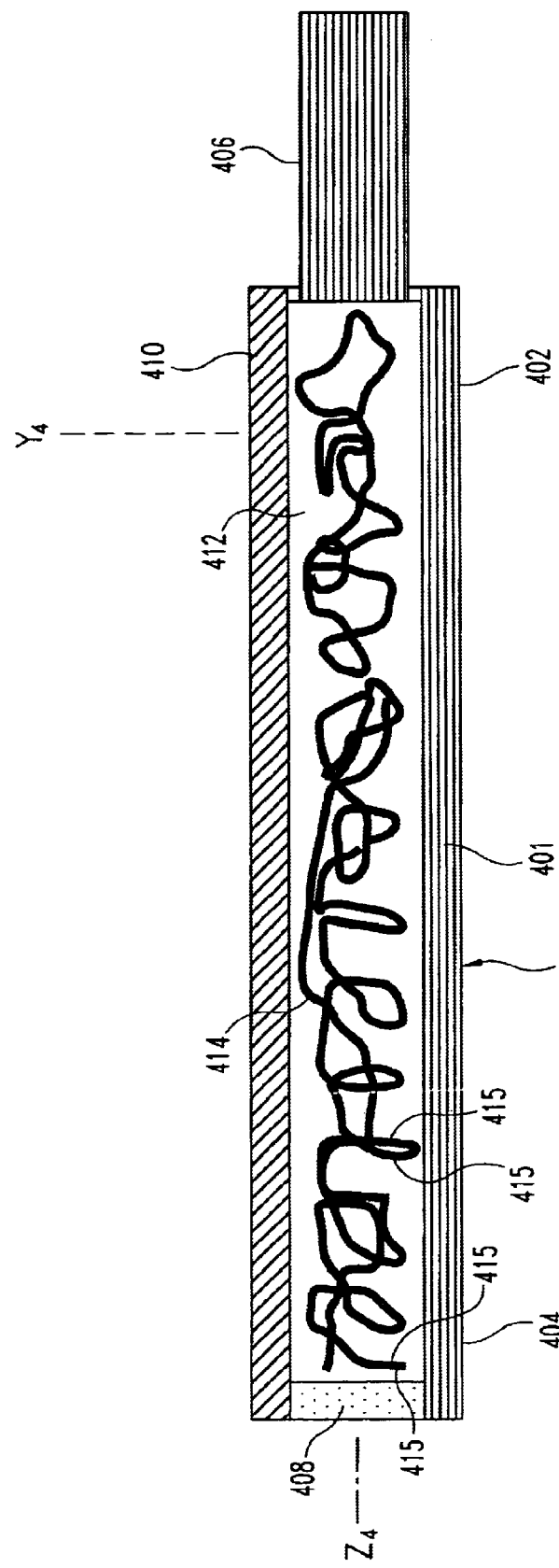
FIG. 10 shows a side cross-sectional view through the $Y_4Z_4$-plane of an optical-sensing element according to a fourth embodiment of the present invention.
Figure 11:
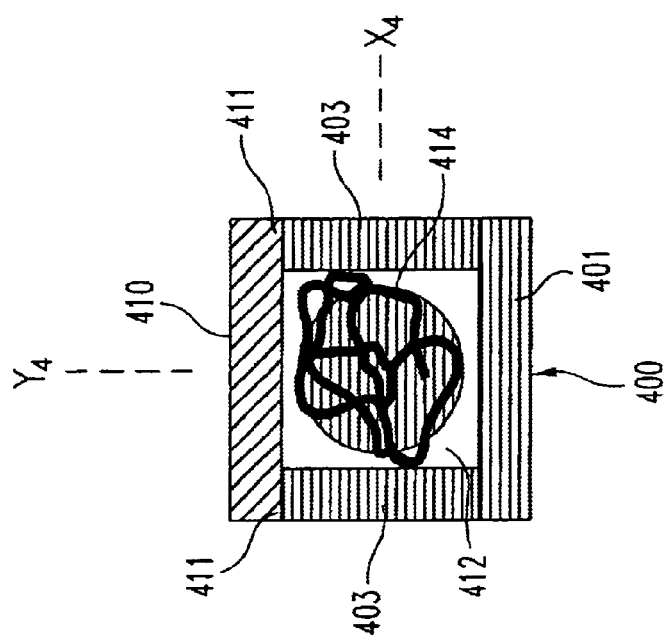
FIG. 11 shows a top cross-sectional view through the $X_4Y_4$-plane of the optical-sensing element illustrated in FIG. 10.
Figure 12:
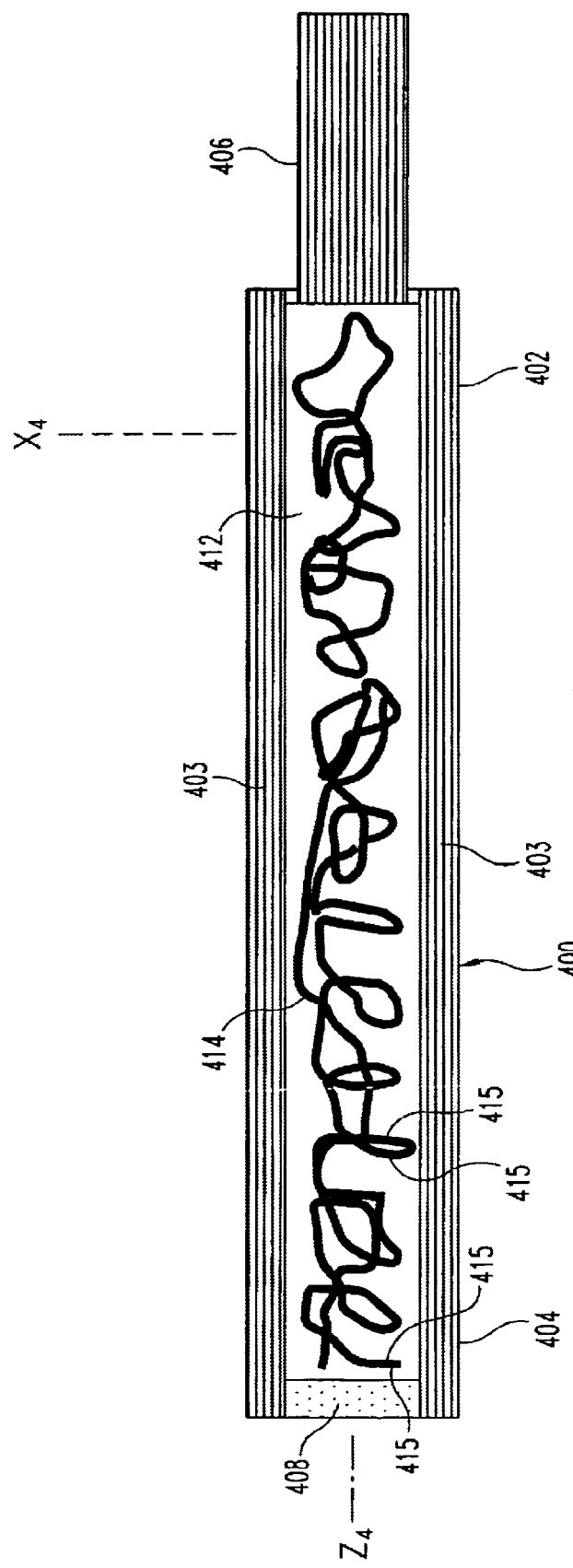
FIG. 12 shows a front cross-sectional view through the $X_4Z_4$-plane of the optical-sensing element illustrated in FIG. 10.

A fourth embodiment of the invention is illustrated in FIGS. 10–12. In this embodiment, the body 400, base portion 401, side walls 403, light-transmitting conduit 406, light-absorbing material 408, membrane 410, edges 411, cavity 412, and respective proximal and distal ends 402 and 404 are as described in the embodiment of FIGS. 1–3. The refractive element 414 comprises a convoluted ribbon or fiber, which provides a plurality of reflective or refractive surfaces 415. The composition, length, width, and thickness of the ribbon 414 can be varied to achieve a packing arrangement which gives optimal amplification of light by multiple reflections off the surfaces 415. The particular composition of the ribbon or fiber is normally not important, as long as suitable reflective or refractive surfaces are provided. Glass or plastic ribbons and fibers are particularly suitable.

Figure 13:
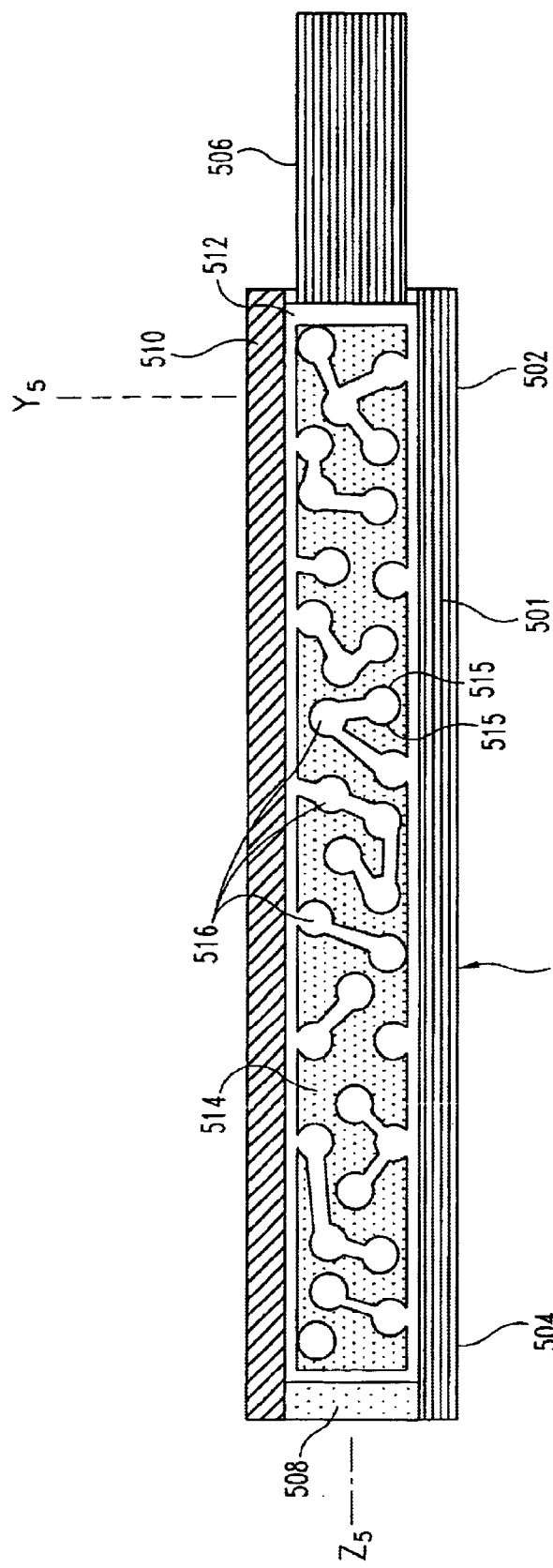
FIG. 13 shows a side cross-sectional view through the $Y_5Z_5$-plane of an optical-sensing element according to a fifth embodiment of the present invention.
Figure 14:
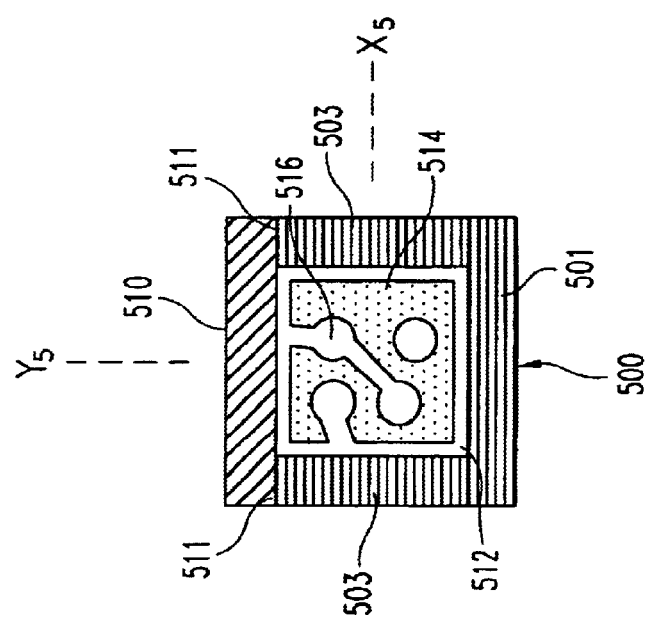
FIG. 14 shows a side cross-sectional view through the $X_5Y_5$-plane of the optical-sensing element illustrated in FIG. 13.
Figure 15:
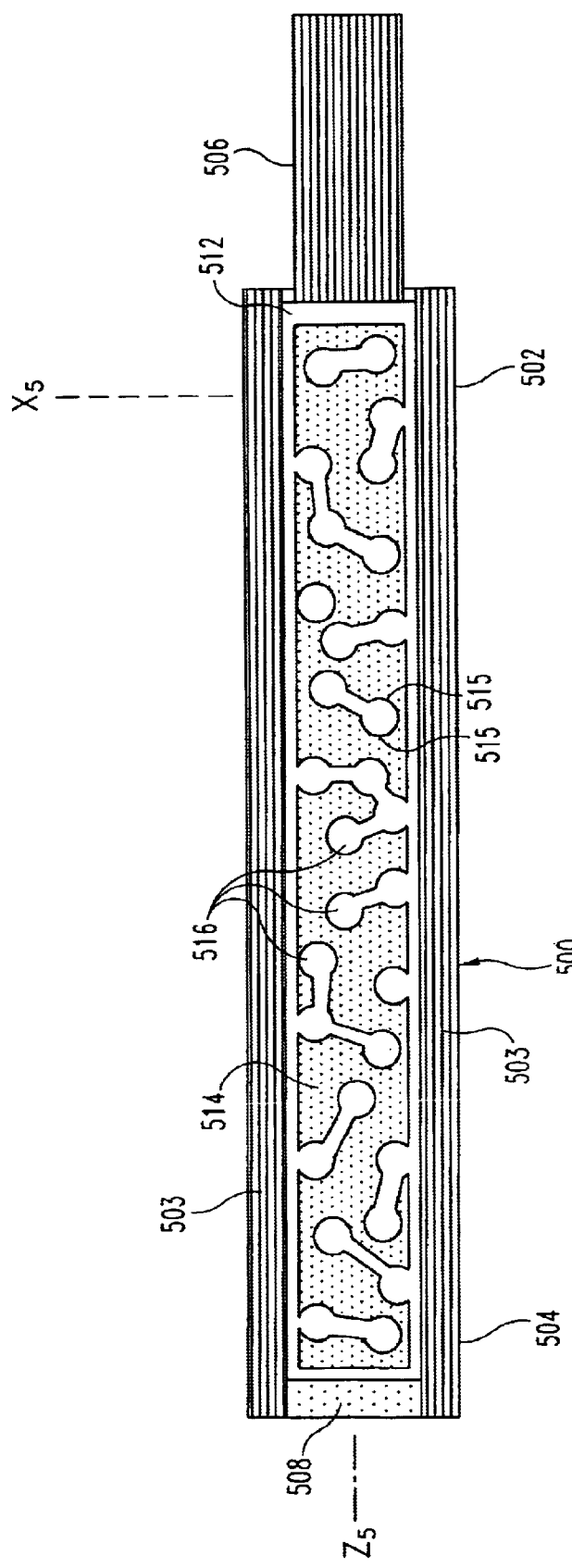
FIG. 15 shows a top cross-sectional view through the $X_5Z_5$-plane of the optical-sensing element illustrated in FIG. 13.

A fifth embodiment of the invention is illustrated in FIGS. 13–15. In this embodiment, the body 500, base portion 501, side walls 503, light-transmitting conduit 506, light-absorbing material 508, membrane 510, edges 511, cavity 512, and respective proximal and distal ends 502 and 504 are as described in the embodiment of FIGS. 1–3. The refractive element 514 comprises a rod, or fiber, having a plurality of pores 516. The pores 516 provide a plurality of reflective or refractive surfaces 515. The rod should have sufficient porosity so that the interior pores are in contact with the analyte. The composition of the rod or fiber, as well as the porosity, pore size and number of pores can be can be varied to achieve optimal amplification of light by multiple reflections off the surfaces 515. The particular composition of the rod or fiber is normally not important, as long as suitable reflective or refractive surfaces are provided. Glass or plastic rods and fibers are particularly suitable.

Figure 16:
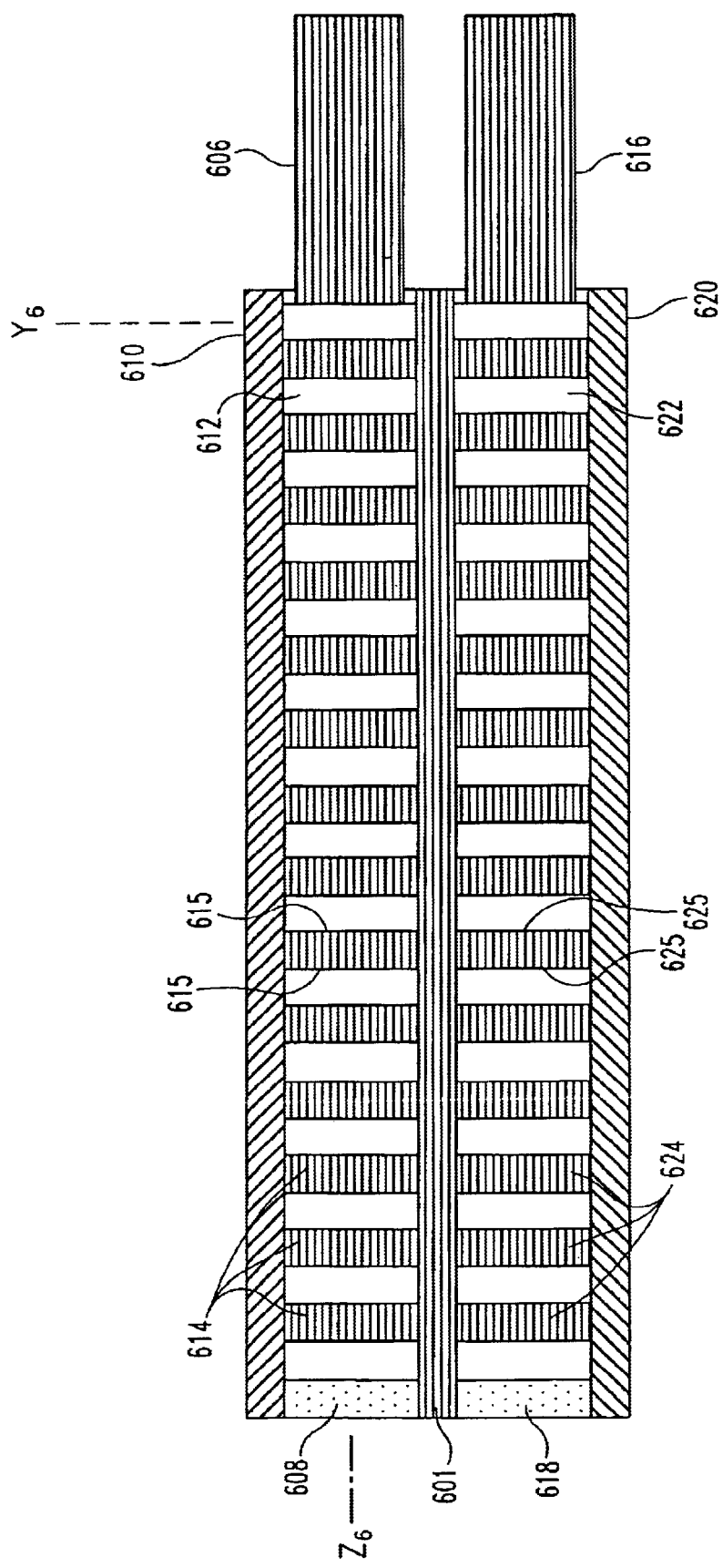
FIG. 16 shows a side cross-sectional view through the $Y_6Z_6$-plane of an optical-sensing element according to a sixth embodiment of the present invention.
Figure 17:
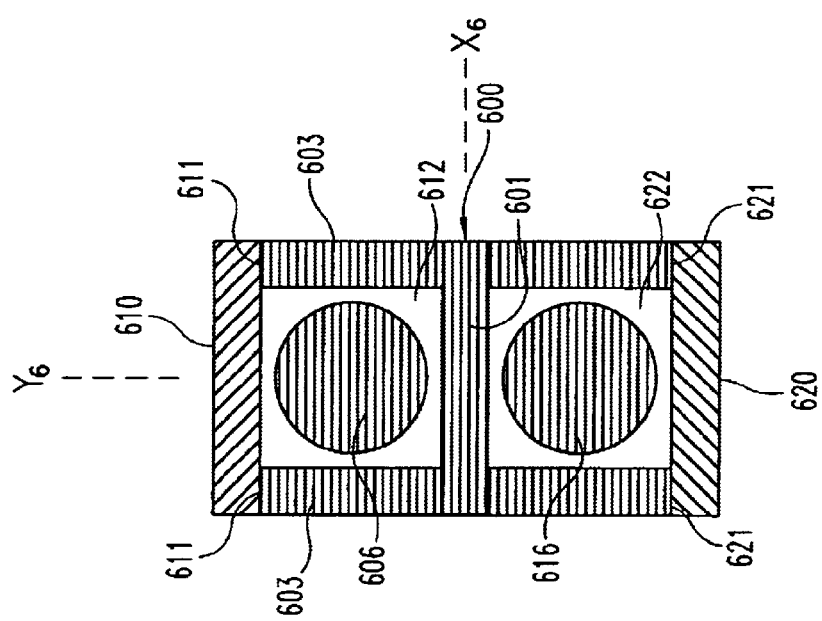
FIG. 17 shows a side cross-sectional view through the $X_6Y_6$-plane of the optical-sensing element illustrated in FIG. 16.
Figure 18:
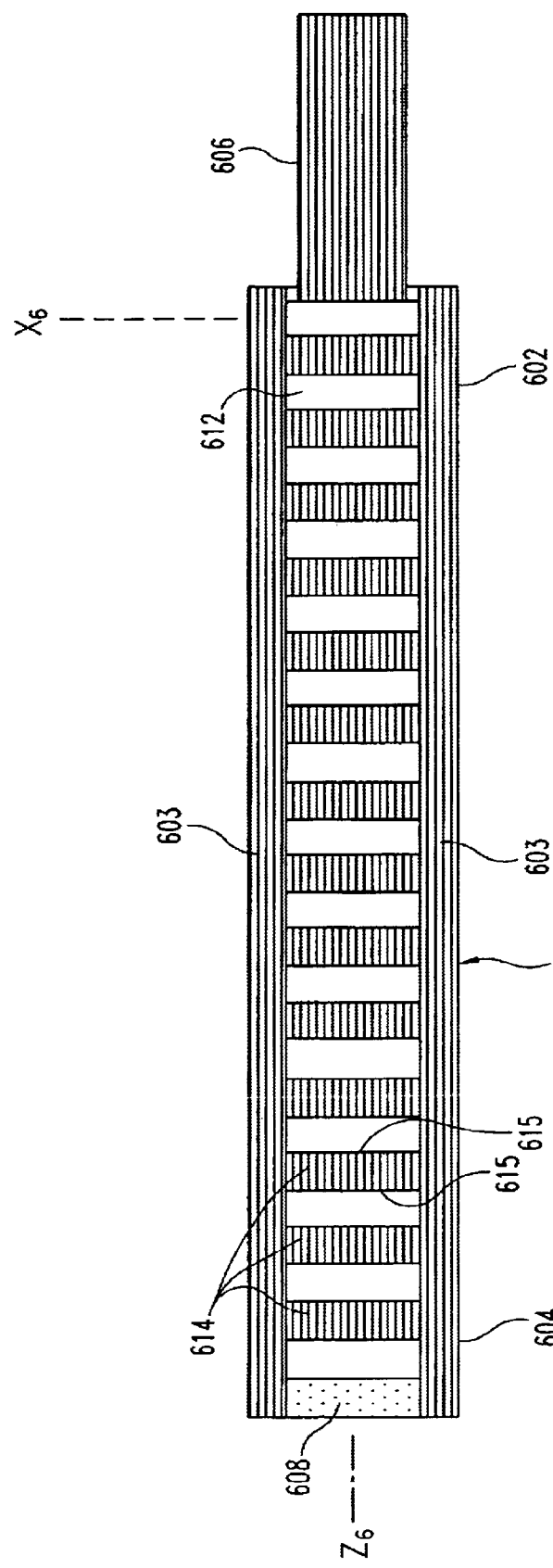
FIG. 18 shows a top cross-sectional view through the $X_6Z_6$-plane of the optical-sensing element illustrated in FIG. 16.

A sixth embodiment of the invention is illustrated in FIGS. 16–18. The body 600 includes a cross-beam portion 601 and two opposing side walls 603, and has an "⊢⊣"-shaped cross-section, preferably manufactured by a plastic molding process. Each of the side walls 603 includes an upper edge 611 and a lower edge 621. The cross-beam portion 601 is attached to each side wall 603 between the upper edge 611 and the lower edge 621. A first semi-permeable membrane 610 is attached to each upper edge 611 of the side walls 603, thereby defining a first cavity 612. A first light-transmitting conduit 606, here a single optical fiber, is sealed in an orifice in the proximal end 602 of the body 600 adjacent the first cavity 612. The distal end 604 of the body 600 preferably comprises a first light-absorbing material 608 adjacent the first cavity 612. A second semi-permeable membrane 620 is attached to each lower edge 621 of the opposing walls 603 of the body 600, thereby forming a second cavity 622 superposed with respect to the first cavity 612. A second light-transmitting conduit 616, here a single optical fiber, is sealed in an orifice in the proximal end 602 of the body 600 adjacent the second cavity 622. The distal end 604 of the body 600 preferably comprises a second light-absorbing material 618 adjacent the second cavity 622. The first and second cavities include first and second refractive elements 614, 624. The refractive elements preferably are made from the same material as the body 600 and comprise a plurality of substantially parallel, rectangular plates as before. The first and second light-absorbing materials, 608 and 618 respectively, preferably have the same composition. The second semi-permeable membrane 620 may have the same composition as its counterpart in the first cavity 612, or a different composition.

Figure 19:
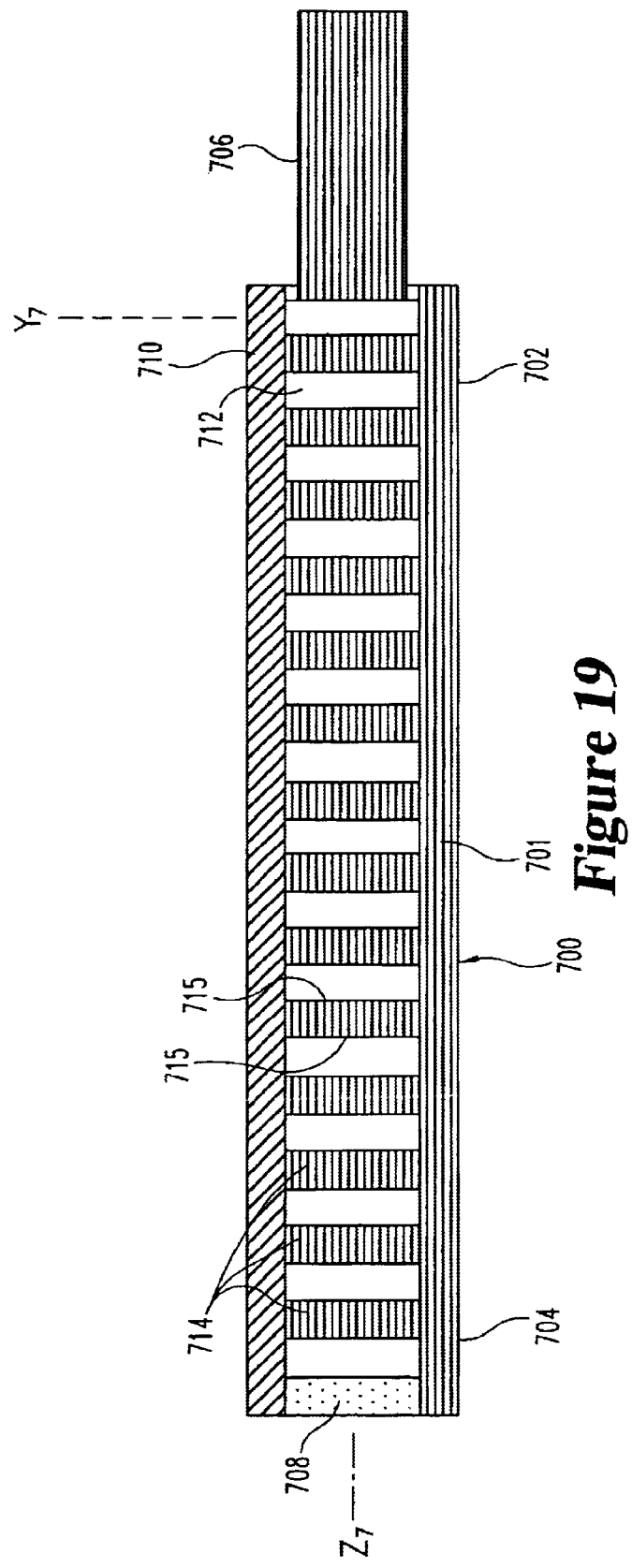
FIG. 19 shows a side cross-sectional view through the $Y_7Z_7$-plane of an optical-sensing element according to a seventh embodiment of the present invention.
Figure 20:
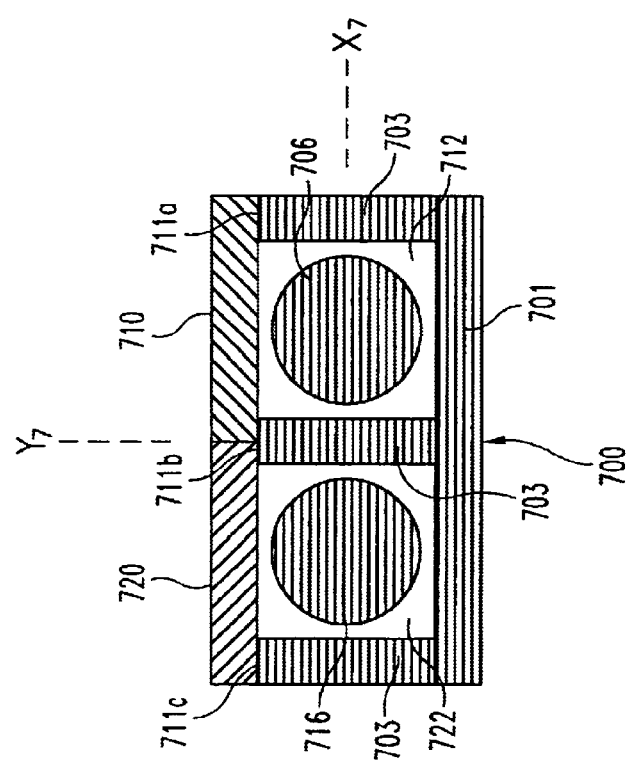
FIG. 20 shows a side cross-sectional view through the $X_7Y_7$-plane of the optical-sensing element illustrated in FIG. 19.
Figure 21:
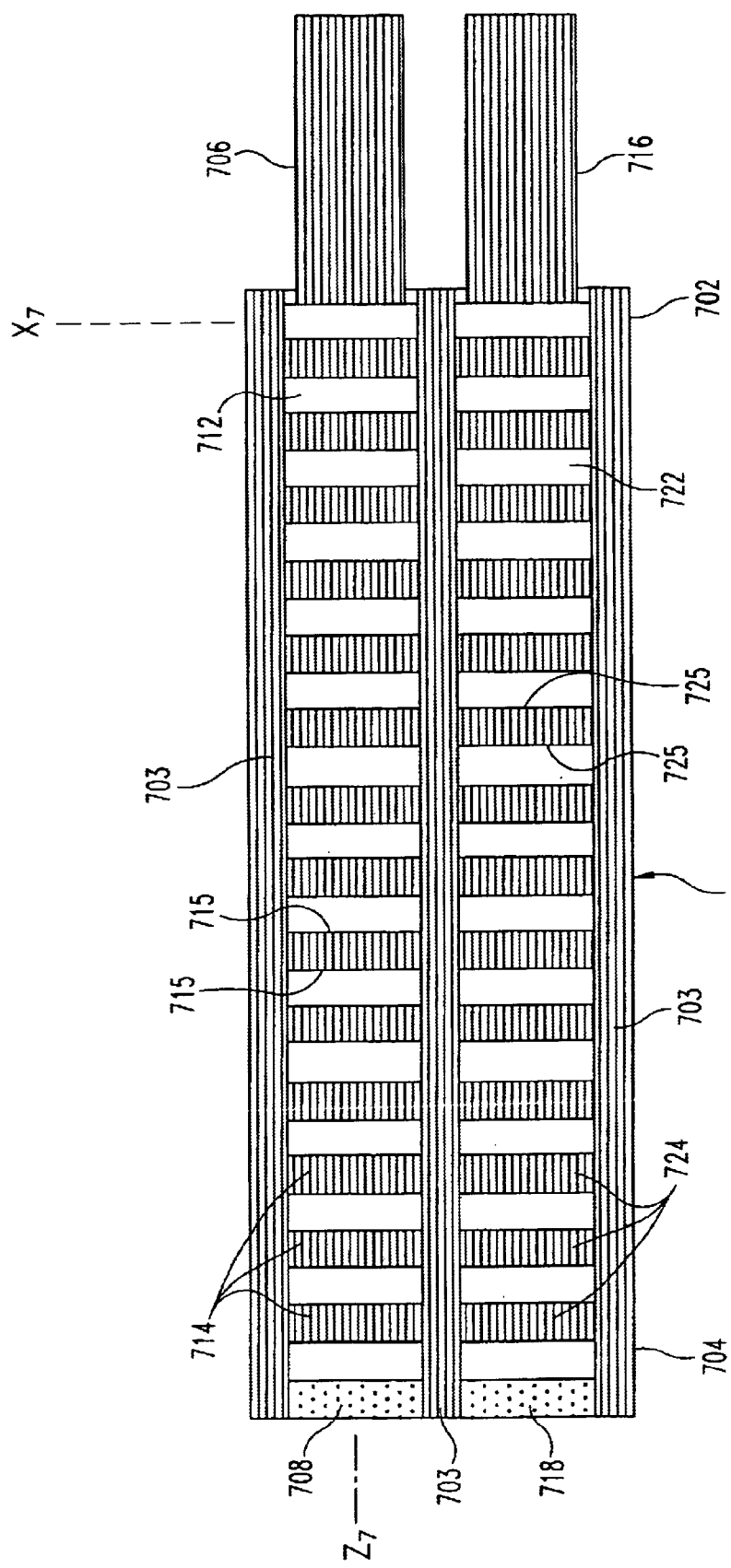
FIG. 21 shows a top cross-sectional view through the $X_7Z_7$-plane of the optical-sensing element illustrated in FIG. 19.

A seventh embodiment of the invention is illustrated in FIGS. 19–21. The body 700 of the sensing element has a "⊔" shaped cross-section, preferably manufactured by a plastic molding process. The body has a base portion 701 and three opposing side walls 703. Each of the side walls 703 includes an upper edge 711a–711c. The body 700 has a proximal end 702 and a distal end 704, and is preferably less than 2 mm in length. A first semi-permeable membrane 710 is attached to the upper edge 711a of one of the outer side walls 703 and to the upper edge 711b of the inner side wall 703, thereby defining a first cavity 712. A first light-transmitting conduit 106, here a single optical fiber, is sealed in an orifice in the proximal end 702 of the body 700 adjacent the first cavity 712. The distal end 704 of the body 700 preferably comprises a first light-absorbing material 708 adjacent the first cavity 712. The first cavity 712 contains a first refractive element 714. The first refractive element 714 is preferably made from the same material as the body 700, and comprises a plurality of substantially parallel, rectangular plates.

A second semi-permeable membrane 720 is attached to the upper edge 711c of the other outer side wall 703 and to the upper edge 711b of the inner side wall 703, thereby forming a second cavity 722. The second cavity 722 is in side-by-side orientation with respect to the first cavity 712. A second light-transmitting conduit 716, here a single optical fiber, is sealed in an orifice in the proximal end 702 of the body 700 adjacent the second cavity 722. The distal end 704 of the body 700 preferably comprises a second light-absorbing material 718 adjacent the second cavity 722. The second cavity 722 contains a second refractive element 724. The second refractive element 724 is preferably made from the same material as the body 700, and comprises a plurality of substantially parallel, rectangular plates. The first and second light-absorbing materials, 708 and 718 respectively, preferably have the same composition. The second semi-permeable membrane 720 may independently have the same composition as its counterpart in the first cavity 712, or a different composition.

The sixth and seventh embodiments of this invention are particularly useful for simultaneously measuring the concentration of two different analytes in a biological matrix. This may be accomplished by choosing respective semi-permeable membranes that are permeable to different species. For example, the first semi-permeable membrane could be permeable to analyte A but impermeable to analyte B, while the second semi-permeable membrane could be permeable to analyte B but impermeable to analyte A. The first cavity would then be used to monitor the concentration of analyte A, while the second cavity would be used to monitor the concentration of analyte B.

The sixth and seventh embodiments of this invention may also be useful for correcting for background changes in the refractive index of a biological matrix resulting from variations in physical parameters like temperature. For example, the first semi-permeable membrane could be permeable to only analyte A, while the second semi-permeable membrane could be impermeable to all of the components (analytes) of the biological matrix. The first cavity would then constitute a sample cell, while the second cavity would constitute a reference cell. The sample cell could be used to monitor changes in light resulting from changes in the concentration of analyte A and physical changes in the environment of the sensing element. The reference cell could be used to monitor changes in light intensity resulting solely from physical changes in the environment of the biological matrix. The differences in light intensity between the sample and reference cells would then correlate to the change in refractive index of the biological matrix due solely to a change in concentration of analyte A.

Alternatively, the first semi-permeable membrane could be permeable to analyte A and background species in the biological matrix, while the second semi-permeable membrane could be permeable to the background species but impermeable to analyte A. The first cavity would still constitute a sample cell, while the second cavity would constitute a reference cell. However, the sample cell would now be used to monitor changes in light intensity resulting from changes in the concentration of analyte A, physical changes in the environment of the sensing element, and changes in the concentration of the background species. Similarly, the reference cell would be used to monitor changes in light intensity resulting from physical changes in the environment of the sensing element and changes in the concentration of the background species. The difference in light intensity between the sample and reference cells would correlate with the change in refractive index of the biological matrix due to a change in concentration of analyte A.

The implantable analyte sensor of the present invention is designed to optically couple with an opto-electronic detection and measurement assembly. The opto-electronic detection and measurement assembly may include the light source for transmitting light from the light source to the sensing element, or alternatively, the light source may comprise a separate assembly. The opto-electronic detection and measurement assembly includes a detector for receiving light that has been returned or otherwise reflected from the sensing element. A signal-processing and computing element is optically coupled to the detector to compare the intensity of the received light to that of the transmitted light. By using previously measured reference values, the signal-processing and computing element converts the differences in light intensity to a signal relating to analyte concentration. The signal can then be displayed on a readout device.

The method does not require spectroscopic measurement at one or more defined wavelengths, although in certain cases it might be advantageous to use multiple wavelengths. When measurement at multiple defined wavelengths is not desired, relatively inexpensive opto-electronic components, such as light emitting diodes (LED's), laser diodes, xenon and metal halide lamps, can be used as the light source.

Figure 22:
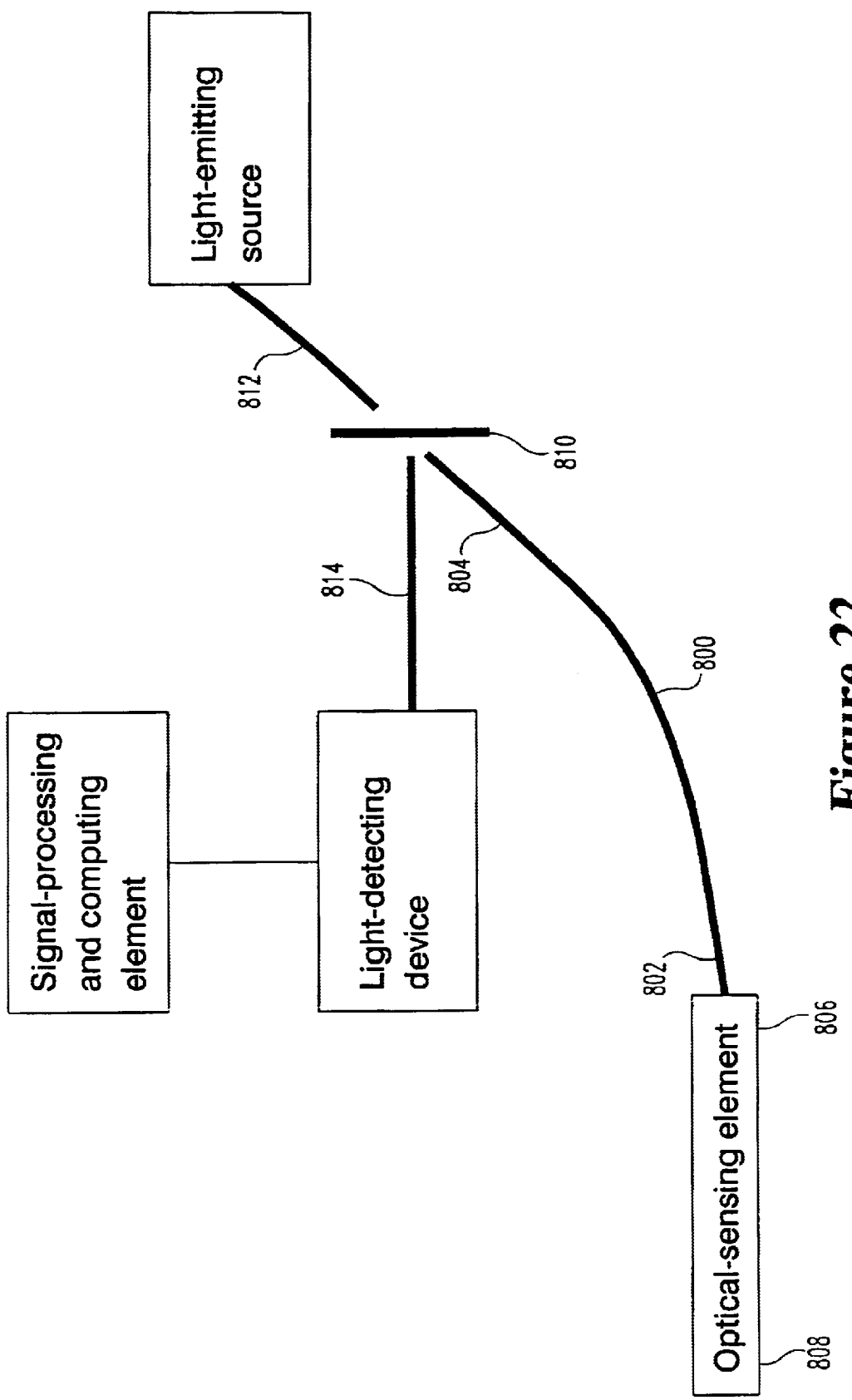
FIG. 22 shows a block diagram of the an opto-electronic detection and measurement assembly optically coupled to an optical-sensing element of the type described in embodiments 1–5.

A block diagram of an opto-electronic detection and measurement assembly optically coupled to an optical-sensing element of the type described in embodiments 1–5 is shown in FIG. 22. The first end 802 of a first light-transmitting conduit 800 is optically coupled to the proximal end 806 of the body of the optical-sensing element 808, for example by sealing the end 802 in an orifice using an adhesive. The second end 804 of the first light-transmitting conduit 800 is optically coupled to both a light-emitting source and a light-detecting device. In this diagram, optical coupling is provided by a beam-splitter 810. The beam-splitter is preferably tilted such that the angle of incoming light is equal to the angle of reflected light, and is oriented such that secondary light emitted from the second end 804 of the first light-emitting conduit 800 is directed into a second light-transmitting conduit 814 connected to a light-detecting device. The light-detecting device can be, for example, a photomultiplier tube or a photodiode. The beam-splitter 810 is also oriented such that primary light emitted from a third light-transmitting conduit 812 connected to the light-emitting source is directed into the second end 804 of the light-transmitting conduit 800. The source can emit light either continuously or in a pulsed mode. Suitable light sources and detectors can be purchased from Hamamatsu Corporation, Bridgewater N.J. The light-detecting device is electrically coupled to a signal-processing and computing element which converts the secondary light to an electronic signal that can be read in conventional fashion, such as by visual display on a conventional readout device. The signal-processing and computing element may comprise, for example, a conventional controller such as a software-driven computer.

Preferably, each of the first, second, and third light-transmitting conduits, 800, 814, and 812 respectively, comprises one or more optical fibers. Suitable optical fibers and optical fiber bundles can be purchased from Polymicro Technologies, LLC of Phoenix, Ariz. Suitable beamsplitters for optical fibers can be purchased from Oz Optics LTD. of Carp, Ontario, Canada.

Figure 23:
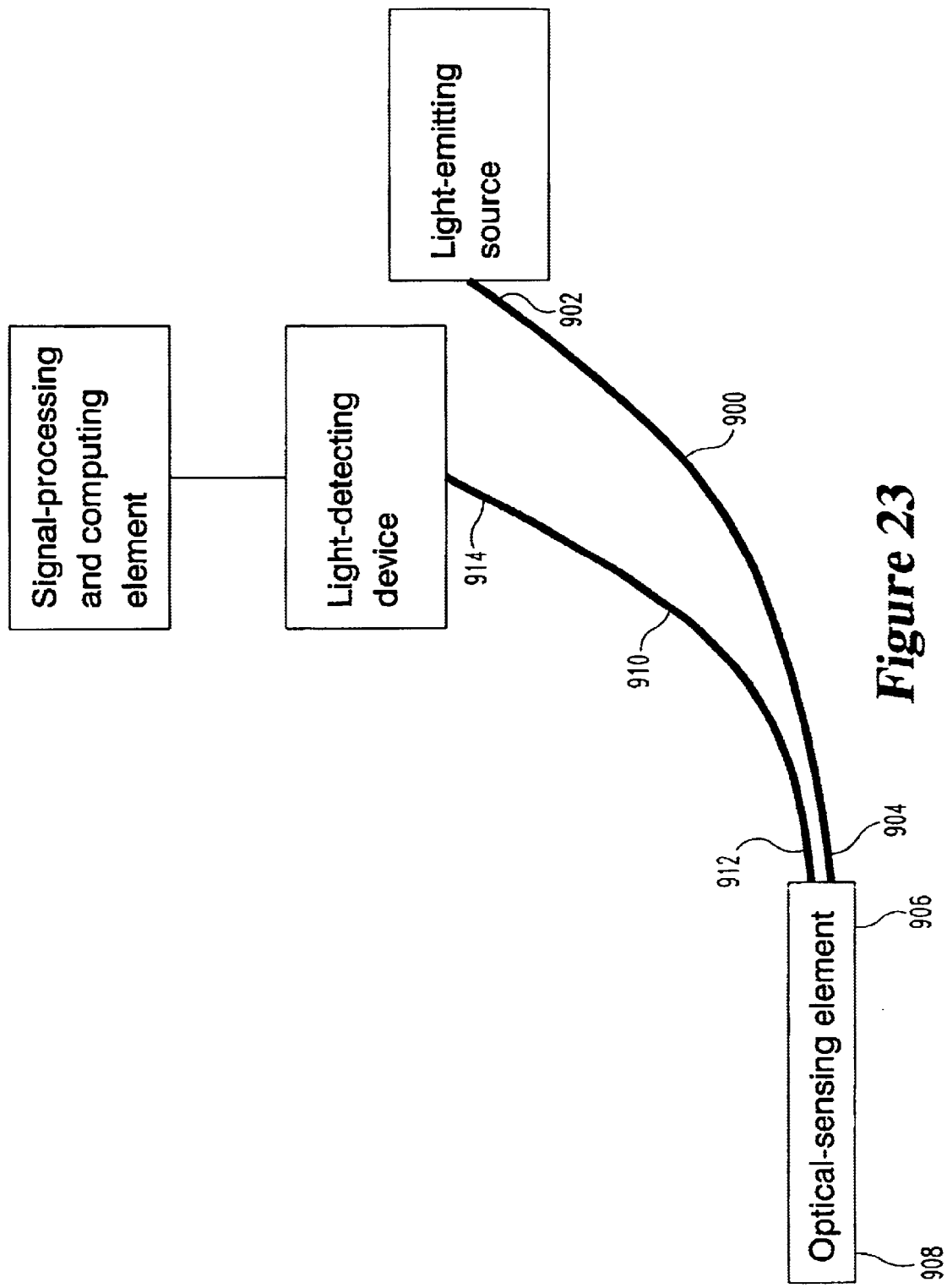
FIG. 23 shows another block diagram of the an opto-electronic detection and measurement assembly optically coupled to an optical-sensing element of the type described in embodiments 1–5.

Another block diagram of an opto-electronic detection and measurement assembly optically coupled to an optical-sensing element of the type described in embodiments 1–5 is shown in FIG. 23. In this arrangement, primary light is emitted from a light-emitting source. The light-emitting source is optically coupled to the first end 902 of a first light-transmitting conduit 900, for example using a standard SMA connector. The second end 904 of the first light-transmitting conduit 900 is optically coupled to the proximal end 906 of the body of the optical-sensing element, for example, by sealing the end 904 in an orifice in the body of the sensing element. The alignment should be such that the primary light is directed into the cavity toward the refractive element. Secondary light resulting from reflection or refraction at the refractive element is collected in the first end 912 of a second light-transmitting conduit 910, which is optically coupled to the proximal end 906 of the body of the optical-sensing element. The second end of the conduit 914 is optically coupled to a light-detecting device, for example using an SMA connector. The light-detecting device can be, for example, a photomultiplier tube or a photodiode. Preferably, each of the first and second light-transmitting conduits, 900 and 910 respectively, comprises one or more optical fibers. The light-detecting device is electrically coupled to a signal-processing and computing element, which converts the secondary light to an electronic signal, which can be displayed on a readout device.

Figure 24:
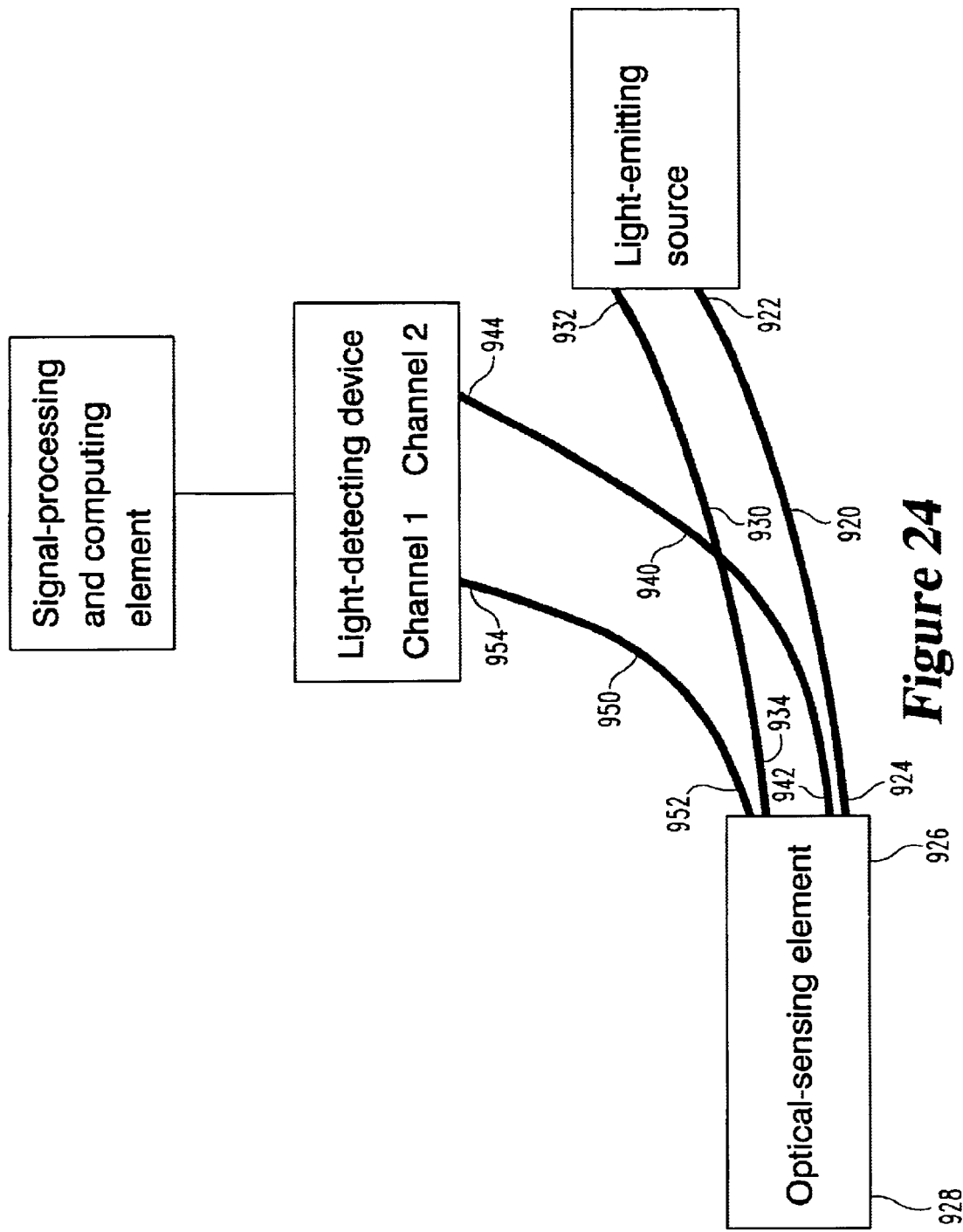
FIG. 24 shows a block diagram of an opto-electronic detection and measurement assembly optically coupled to an optical-sensing element of the type described in embodiments 6–7.

A block diagram of an opto-electronic detection and measurement assembly optically coupled to an optical-sensing element of the type described in embodiments 6–7 is shown in FIG. 24. Primary light is emitted from a light-emitting source. The light-emitting source is optically coupled to the first end 922 of a first light-transmitting conduit 920. The second end 924 of the first light-transmitting conduit 920 is optically coupled to the proximal end 926 of the body of the optical-sensing element adjacent the first cavity, in an alignment such that the primary light is directed into the first cavity toward the first refractive element. Secondary light resulting from reflection or refraction at the first refractive element is collected in the first end 942 of a second light-transmitting conduit 940. The first end 942 of the second light-transmitting conduit 940 is optically coupled to the proximal end 926 of the body of the optical-sensing element adjacent the first cavity, while the second end 944 is optically coupled to a channel of a light-detecting device. The light-detecting device can be, for example, a photomultiplier tube or a photodiode.

In addition, the light-emitting source is optically coupled to the first end 932 of a third light-transmitting conduit 930. The second end 934 of the third light-transmitting conduit 930 is optically coupled to the proximal end 926 of the body of the optical-sensing element adjacent the second cavity, in an alignment such that the primary light is directed into the second cavity toward the second refractive element. Secondary light resulting from reflection or refraction at the second refractive element is collected in the first end 952 of a fourth light-transmitting conduit 950. The first end 952 of the fourth light-transmitting conduit 950 is optically coupled to the proximal end 926 of the body of the optical-sensing element adjacent the second cavity, while the second end 954 of the fourth light-transmitting conduit 950 is optically coupled to a second channel of the light-detecting device. Preferably, each of the first, second, third and fourth light-transmitting conduits, 920, 940, 930, and 950 respectively, comprises one or more optical fibers. The light-detecting device is electrically coupled to a signal-processing and computing element, which converts the secondary light to an electronic signal, which can be displayed on a readout device.

The invention further contemplates a method of measuring the concentration of an analyte in a biological matrix. First, an optical-sensing element is inserted in the matrix. The optical-sensing element includes a body, a semi-permeable membrane and a refractive element as described previously. Next, primary light is transmitted from a light-emitting source to the body of the optical-sensing element, and directed into the cavity to the refractive element. Then, secondary light resulting from the reflection or refraction of the light at the refractive element is collected and read by a light-detecting device. The difference in intensity between the transmitted light and the reflected light is measured by a standard computing device, and the analyte concentration in the biological matrix is determined by the computing device using, for example, an algorithm and calibration procedure. Such evaluation algorithms and calibration procedures are well known to those of ordinary skill in the art.

Once the analyte concentration in the biological matrix has been derived, the measurement process can be repeated, thereby allowing for continuous monitoring of the analyte concentration. Alternatively, the measurement can be made at specific or random intervals in time. In either case, the results can be displayed using means known to those of ordinary skill in the art. For instance, a running graph/chart of the analyte concentration can be displayed on a monitor. Alternatively, the analyte concentration can be displayed on a digital readout device or an analog gauge. Moreover, the electronic signal can be used to trigger an alarm on an audio device when the analyte concentration is outside a given range.

It is a characteristic of the invention that changes in light intensity returned from the optical sensing component can be related to changes in the concentration of a specified analyte, such as glucose, in the biological matrix without the necessity of spectroscopic measurement at multiple wavelengths. In addition, there is no requirement that two detection measurements be made, wherein at least one of the detection measurements is a spatially resolved measurement of multiply reflected light. All measurements of light intensity returned from the optical sensing component can be made at the same spatial location. In addition, the principle relied on is light reflection, not optical absorption. Thus, in contrast to previously know spectroscopic methods (particularly NIR spectroscopy), the wavelength is preferably chosen in a region of the spectrum where absorption of the analyte is relatively low.

Spectral regions where the absorption of glucose is relatively low are described, for example, in U.S. Pat. No. 5,551,422. Preferably, the wavelength is between 400 nm and 1300 nm. Other wavelengths outside of this range may be utilized in suitable cases, provided that interfering species are not substantially present in the matrix, or if present, are compensated for by the use of proper reference test samples.

In contrast to prior techniques, these spectral regions need not normally be further narrowed to avoid interferences due to absorption by other components in the biological matrix (e.g., hemoglobin), since the semi-permeable membrane excludes such components from the sensing volume. Likewise, there is no particular preference for relatively short wavelengths because the method does not depend on the depth of penetration of light into the biological matrix.

In contrast to absorption-based methods for noninvasive analytical determination of the glucose concentration in a biological matrix, in the present invention it is generally not necessary to use narrow-band measurement, due to the minimal dependence on the measurement wavelength. Thus, relatively broad-banded light sources (with half-widths larger than 20 nm), such as light-emitting diodes (LED's) and other semi-conductor light sources, can be used without the need for subsequent spectral selection on the primary side or secondary side. This considerably reduces the cost of the apparatus. This feature makes the apparatus especially suitable for the continuous monitoring of the glucose concentration of a diabetic. Even though it is generally not necessary to use a laser as a primary light source, in some situations, such as with planar refractive surfaces, laser light may be utilized if desired. Similarly, it is generally not necessary to use coherent or polarized light.

An alternative arrangement to that described above utilizes one or more light sources that emit light into the cavity at defined wavelengths in order to exploit the dispersion (i.e., wavelength-dependence) of the refractive indices of the refractive material and/or the analyte. In this arrangement, a light source emits light having a wavelength $\lambda_1$ at which the refractive index of the refractive element $n_{element}$ is always greater than the refractive index of the analyte $n_{analyte}$. Another light source emits light having a wavelength $\lambda_2$ at which the refractive index of the refractive element $n_{element}$ is always less than the refractive index of the analyte $n_{analyte}$. The relative index of refraction $n_{rel}=n_{analyte}/n_{element}$ at each wavelength is as follows:

$n_{rel}<1$ for $\lambda_1$, and $n_{rel}>1$ for $\lambda_2$.

Alternatively, a single light source that emits light at multiple wavelengths may be used in combination with a (dichroic) beam splitter to split the light into separate beams at the desired wavelengths.

When the concentration of the analyte changes, for example increases, $n_{analyte}$ increases and therefore $n_{rel}$ increases for both $\lambda_1$ and $\lambda_2$. In this setting the relative change in the signals caused by $\lambda_1$ and $\lambda_2$ is being measured.

A relative measurement does not rely on an absolute calibration and is less affected by background considerations. Hence this arrangement can be used to improve the sensitivity and/or the specificity of the method.

In implementation of this arrangement using multiple wavelengths, either a single detector or multiple detectors can be used. For example, when two wavelengths $\lambda_1$ and $\lambda_2$ are used as described above, two separate detectors can be utilized to receive the signals. One detector would receive the "$\lambda_1$-light" and the other would receive the "$\lambda_2$-light". If desired, a wavelength-dependent dicroic beam splitter can be used to isolate the proper wavelength from the reflected light. A controller could then be utilized to analyze the signals by means such as signal subtraction to yield an analyte-dependent result. A single detector may also be utilized, however in this instance, the signals are generally received alternating in time.

Suitable light sources for use in this multiple wavelength approach include multiple independent single light sources each having a different wavelength. Alternatively, a beam splitter may be utilized with a single, multichromatic light source to split the light into separate beams at different, well-defined wavelengths.

The sensor could be designed as a transcutaneous sensor, which uses a light guide to transmit light to and from the optical-sensing element. Alternatively, the sensor could be an integrated device. In this case, the implanted device would incorporate the light-emitting and optical-sensing elements in a single element. A fully compatible sensor unit can also include RF data transmission means and a battery charge.

Obviously, numerous modifications and variations of the present invention are possible in light of the above teachings. It is therefore to be understood that within the scope of the appended claims, the invention may be practiced otherwise than as specifically described herein.

What is claimed is:

1. An assembly for measuring the concentration of an analyte in a biological matrix, comprising: an implantable optical-sensing element comprising a body; a first semi-permeable membrane mounted on said body, said first semi-permeable membrane being permeable to said analyte, and impermeable to background species in said biological matrix, said first membrane and said body aligned to define a first cavity; a first refractive element disposed in said first cavity; a second membrane mounted on said body remote from said first membrane, said second membrane and said body aligned to define a second cavity; and a second refractive element disposed in said second cavity;
   a source for providing light into each of said first and second cavities toward said respective first and second refractive elements;
   a detector for receiving light from each of said first and second cavities; and
   a signal-processing and computing element optically coupled to said detector for relating said received light to a concentration of said analyte.

2. The assembly of claim 1, wherein said analyte comprises a first analyte, said first semi-permeable membrane being permeable to said first analyte and impermeable to a second analyte, and wherein said second membrane is permeable to said second analyte.

3. The assembly of claim 2, wherein said second membrane is impermeable to said first analyte.

4. The assembly of claim 3, wherein said second membrane is impermeable to said analyte.

5. The assembly of claim 1, wherein said source comprises a light transmitter for transmitting light into each of said first and second cavities.

6. The assembly of claim 5, wherein said transmitted light has a wavelength between 400 and 1300 nm.

7. The assembly of claim 1, wherein said detector comprises first and second channels, said first channel receiving light reflected from said first refractive element, and said second channel receiving light reflected from said second refractive element.

8. The assembly of claim 1, wherein said received light is convertible by signal-processing and computing element into an electronic signal.

9. The assembly of claim 8, said assembly further comprising a readout device for display of said electronic signal.

10. The assembly of claim 9, wherein said readout device comprises an analog, digital or audio readout.

11. The assembly of claim 1, wherein said body has a "⊔⊔"-shaped cross-section.

12. The assembly of claim 1, wherein said body has a "⊢⊣"-shaped cross-section.

13. An implantable optical-sensing element suitable for measuring the concentration of an analyte in a biological matrix, said optical-sensing element comprising: a body a first semi-permeable membrane mounted on said body, said first semi-permeable membrane being permeable to said analyte, and impermeable to background species in said biological matrix, said first membrane and said body aligned to define a first cavity; a first refractive element disposed in said first cavity; a second membrane mounted on said body remote from said first membrane, said second membrane and said body aligned to define a second cavity isolated from said first cavity; and a second refractive element disposed in said second cavity.

14. The optical-sensing element of claim 13, wherein said analyte comprises a first analyte, said first semi-permeable membrane being permeable to said first analyte and impermeable to a second analyte, and wherein said second membrane is permeable to said second analyte.

15. The optical-sensing element of claim 14, wherein said second membrane is impermeable to said first analyte.

16. The optical-sensing element of claim 13, wherein said second membrane is impermeable to said analyte.

17. The optical-sensing clement of claim 13, wherein said body has a "⊔⊔"-shaped cross-section.

18. The optical-sensing element of claim 13, wherein said body has a "⊢⊣"-shaped cross-section.

19. A method for measuring the concentration of an analyte in a biological matrix, said method comprising:
   implanting an optical-sensing element in said biological matrix, said optical-sensing element comprising a body, a semi-permeable membrane mounted to said body, said semi-permeable membrane being permeable to said analyte, but impermeable to background species in said matrix, said semi-permeable membrane and said body defining a cavity, and a refractive element disposed in said cavity;
   introducing primary light from a light-emitting source into said body of said optical-sensing element, and directing said primary light toward said refractive element;
   collecting secondary light reflected from said optical-sensing element and transmitting said secondary light to a light-detecting device;
   measuring an intensity of said secondary light, and evaluating said analyte concentration in said biological matrix by comparing said measured intensity of said secondary light with an intensity of said primary light.

20. The method of claim 19, wherein said evaluation is carried out by means of an evaluation algorithm and a calibration.

21. The method of claim 19, wherein said analyte comprises glucose, and said primary light has a wavelength in a spectral region wherein glucose has a minimal effect on absorption of said primary light.

22. A method for measuring the concentration of an analyte in a biological matrix, said method comprising
implanting an optical-sensing element in said biological matrix, said optical-sensing element comprising a body, a first membrane mounted to said body, a second membrane mounted on said body remote from said first membrane, at least one of said membranes being permeable to said analyte, but impermeable to background species in said biological matrix, said first and second membranes and said body defining a cavity, and a refractive element disposed in said cavity;
transmitting primary light from a light-emitting source into said cavity toward said refractive element;
collecting secondary light reflected from refractive element, and transmitting said secondary light to a light-detecting device;
measuring an intensity of said secondary light with said light-detecting device;
deriving said analyte concentration in said biological matrix from said measured intensity of said secondary light by means of an evaluation algorithm and a calibration.

23. The method of claim 22, wherein said analyte is glucose, and said primary light has a wavelength in a spectral region wherein glucose has a minimal effect on absorption of said primary light.

24. A method for measuring the concentration of an analyte in a biological matrix, said method comprising:
implanting an optical-sensing element in said biological matrix, said optical-sensing element comprising: a body, a first semi-permeable membrane mounted on said body, a second semi-permeable membrane mounted on said body remote from said first semi-permeable membrane, said first semi-permeable membrane being permeable to said analyte, but impermeable to background species in said biological matrix, said body and said first membrane defining a first cavity, a first refractive element disposed in said first cavity, said body and said second membrane defining a second cavity isolated from said first cavity, and a second refractive element disposed in said second cavity;
transmitting primary light from a light-emitting source to said body, and directing respective streams of said primary light into said first cavity toward said first refractive element, and into said second cavity toward said second refractive element;
collecting light from said body resulting from reflection at said first refractive element and transmitting said light to a first channel of a light-detecting device;
collecting light from said body resulting from reflection at said second refractive element and transmitting said light to a second channel of said light-detecting device;
measuring the intensity of light collected from each of said first and second channels;
computing the concentration of an analyte in said biological matrix by comparing the intensity of the transmitted light and the light collected from each of said first and second channels.

25. The method of claim 24, wherein said analyte comprises a first analyte, said first semi-permeable membrane being permeable to said first analyte and impermeable to a second analyte in said biological matrix, said second membrane being permeable to said second analyte; and wherein said computing step computes the concentration of each of said first and second analytes.

26. An assembly for monitoring the concentration of an analyte in a biological matrix, comprising:
an implantable optical-sensing element, said implantable optical-sensing element comprising: a body; a membrane mounted on said body, said membrane and body defining a cavity for receiving said analyte, said membrane being substantially permeable to said analyte and substantially impermeable to background species an said biological matrix; and a refractive element disposed in said cavity;
a source for providing light of a first wavelength and a second wavelength into said cavity, said refractive element having a refractive index greater than the refractive index of the analyte at the first wavelength, and less than the refractive index of the analyte at the second wavelength;
a detector for receiving from said cavity an intensity of light at each of said first and second wavelengths at a first concentration of said analyte, and for receiving from said cavity an intensity of light at each of said first and second wavelengths at a second concentration of said analyte; and
a signal-processing and computing element optically coupled to said detector for comparing said intensities of light received at said first wavelength to said intensities of light received at said second wavelength, and relating said intensities to analyte concentration.

27. The assembly of claim 26, wherein said source includes abeam splitter for splitting said light into light of at least two wavelengths.

28. The assembly of claim 26, wherein said source comprises at least two light sources, each light source capable of providing light at a defined wavelength.

29. The assembly of claim 26, wherein said detector comprises a detector member for detecting an intensity of light of said first wavelength, and a detector member for detecting light of said second wavelength.

30. A method for monitoring a change in the concentration of an analyte in a biological matrix of a test subject, comprising:
implanting an optical-sensing element in said subject, said implantable optical-sensing element comprising a body; a membrane mounted on said body, said membrane and body defining a cavity for receiving said analyte, said membrane being substantially permeable to said analyte and substantially impermeable to background species in said biological matrix; and a refractive element disposed in said cavity;
transmitting light of a first wavelength and a second wavelength into said cavity, said refractive element having a refractive index greater than the refractive index of the analyte at the first wavelength, and less than the refractive index of the analyte at the second wavelength;
collecting from said cavity an intensity of light at each of said first and second wavelengths at a first concentration of said analyte, and an intensity of light at each of said first and second wavelengths at a second concentration of said analyte; and
measuring said change in concentration of said analyte by comparing said intensities of light received at said first wavelength to said intensities of light received at said second wavelength for each of said first and second concentrations, and relating said intensities to changes in analyte concentration.

* * * * *